(12) United States Patent  
Nilsson et al.

(10) Patent No.: US 7,226,925 B2
(45) Date of Patent: Jun. 5, 2007

(54) COMPOUNDS, THEIR USE AND PREPARATION

(75) Inventors: Björn M. Nilsson, Stockholm (SE); Erik Ringberg, Uppsala (SE); Birger Sjöberg, Sollentuna (SE); Mattias Jönsson, Uppsala (SE)

(73) Assignee: Biovitrum AB, Stockholm (SE)

( * ) Notice: Subject to any disclaimer, the term of this patent is extended or adjusted under 35 U.S.C. 154(b) by 138 days.

(21) Appl. No.: 10/464,422

(22) Filed: Jun. 18, 2003

(65) Prior Publication Data

US 2004/0029888 A1   Feb. 12, 2004

Related U.S. Application Data

(60) Provisional application No. 60/416,701, filed on Oct. 7, 2002, provisional application No. 60/406,119, filed on Aug. 26, 2002.

(30) Foreign Application Priority Data

Jun. 19, 2002 (SE) ..................... 0201881
Aug. 26, 2002 (SE) ..................... 0202516

(51) Int. Cl.
*A61K 39/497* (2006.01)
*A61K 31/4965* (2006.01)
*C07D 401/00* (2006.01)
*C07D 241/04* (2006.01)
*C07D 295/00* (2006.01)

(52) U.S. Cl. ..................... 514/252.11; 514/253.12; 514/255.03; 544/360; 544/394; 544/395

(58) Field of Classification Search ............. None
See application file for complete search history.

(56) References Cited

U.S. PATENT DOCUMENTS 6,465,467 B1 * 10/2002 Nilsson et al. ......... 514/252.11

FOREIGN PATENT DOCUMENTS

| WO | WO 00/76984 A2 | 12/2000 |
| WO | WO 02/40456 A1 | 5/2002 |
| WO | WO 02/40457 A1 | 5/2002 |
| WO | WO 03/000663 A1 | 1/2003 |

OTHER PUBLICATIONS

Beshore and Dinsmore, "Preparation of Substituted Piperazinones via Tandem Reductive Amination—(N,N'-Acyl Transfer)-Cyclization" Organic Letters, vol. 4(7), pp. 1201-1204 (Mar. 2002).*
Crow and Mitchell, "Rational Therapy of Eating Disorders" Drugs, vol. 48(3), pp. 372-379 (1994).*
Monteljo-Gonzales et al, "SSRI-Induced Sexual Dysfunction: Fluoxetine, Paroxetine, Sertraline, and Fluvoxamine in a Prospective, Multicenter, and Descriptive Clinical Study of 344 Patients" J. Sex and Marital Therapy, vol. 23(3), pp. 176-194 (Fall 1997).*
Rosen et al, "Effects of SSRIs on Sexual Function: A Critical Review" J. Clin. Psychopharmacology, vol. 19(1), pp. 67-85 (1999).*
Berendsen, "The role of serotonin in hot flushes" Maturitas, vol. 36, pp. 155-164 (2000).*
Lima et al, "Antidepressants for Cocaine Dependence." The Cochrane Database of Systematic Reviews, issue 2, article No. CD002950 (2003).*
Moreau et al, "5HT2c receptor agonists exhibit antidepressant-like properties in the anhedonia model of depression in rats" European Neuropsychopharmacology, vol. 6(3), pp. 169-175 (1996).*
Jenck et al, "Antiaversive effects of 5HT2c receptor agonists and fluoxetine in a model of panic-like anxiety in rats" European Neuropsychopharmacology, vol. 8(3), pp. 161-168.*
Lumma et al., "Piperazinylpyrazines with Central Serotoninmimetic Activity", 1978, J. Med. Chem., vol. 21(6);536-542.

* cited by examiner

*Primary Examiner*—Zachary C Tucker
(74) *Attorney, Agent, or Firm*—Fish & Richardson P.C.

(57) ABSTRACT

The invention relates to compounds of the general Formula (I):

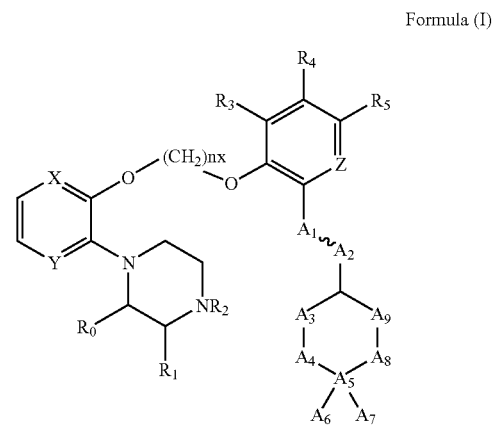

Formula (I)

The compounds may be prepared by per se conventional methods and can be used for treating a human or animal subject suffering from a serotonin-related disorder.

The invention also relates to such use as well as to pharmaceutical compositions comprising a compound of Formula (I).

40 Claims, No Drawings

COMPOUNDS, THEIR USE AND PREPARATION

RELATED APPLICATIONS

This application claims priority to Swedish application number 0201881-0, filed on Jun. 19, 2002, Swedish application number 0202516-1, filed on Aug. 26, 2002, U.S. provisional application No. 60/406,119, filed on Aug. 26, 2002, and U.S. provisional application No. 60/416,701, filed on Oct. 7, 2002, the contents of which are incorporated herein by reference.

FIELD OF THE INVENTION

The present invention relates to novel compounds, to pharmaceutical compositions comprising the compounds, to processes for their preparation, as well as to the use of the compounds for the preparation of a medicament which particularly acts on the central nervous system.

BACKGROUND OF THE INVENTION

Many disorders and conditions of the central nervous system are influenced by the adrenergic, the dopaminergic, and the serotonergic neurotransmitter systems. For example, serotonin has been implicated in a number of disorders and conditions which originate in the central nervous system. A number of pharmacological and genetic experiments involving receptors for serotonin strongly implicate the 5-$HT_{2C}$ receptor subtype in the regulation of food intake (see e. g., Obes. Res. 1995, 3, Suppl. 4, 449S–462S, Diabetes, Obesity and Metabolism 1999, 1, 207–214, and Drugs Future 2001, 26, 383–393). The 5-$HT_{2C}$ receptor subtype is transcribed and expressed in hypothalamic structures associated with appetite regulation. It has been demonstrated that the 5-$HT_{2C}$ receptor agonist m-chlorophenyl-piperazine (mCPP), which has some preference for the 5-$HT_{2C}$ receptor, reduces food intake in mice that express the normal 5-$HT_{2C}$ receptor while the compound lacks activity in mice expressing the mutated inactive form of the 5-$HT_{2C}$ receptor (Nature 1995, 374, 542–546). In a recent clinical study, a slight but sustained reduction in body weight was obtained after 2 weeks of treatment with mCPP in obese subjects (Psychopharmacology 1997, 133, 309–312). Recently, a series of pyrrolo[3,2,1-ij]quinoline derivatives was identified to be 5-$HT_{2C}$ receptor agonists having selectivity over the 5-$HT_{2A}$ receptor (Isaac M., et al., Bioorg. Med. Chem. Lett. 2000, 10, 919–921). The compounds are said to offer a novel approach to the treatment of obesity and epilepsy.

Body weight reduction has also been reported from clinical studies with other "serotonergic" agents (see e.g. IDrugs 1998, 1, 456–470). For example, the 5-HT reuptake inhibitor fluoxetine and the 5-HT releasing agent/reuptake inhibitor dexfenfluramine have exhibited weight reduction in controlled studies. However, currently available drugs that increase serotonergic transmission appear to have only a moderate and, in some cases, transient effects on the body weight.

The 5-$HT_{2C}$ receptor subtype has also been suggested to be involved in CNS disorders such as depression and anxiety (Exp. Opin. Invest. Drugs 1998, 7, 1587–1599; IDrugs, 1999, 2, 109–120).

The 5-$HT_{2C}$ receptor subtype has further been suggested to be involved in urinary disorders such as urinary incontinence (IDrugs, 1999, 2, 109–120).

Compounds which have a selective effect on the 5-$HT_{2C}$ receptor may therefore have a therapeutic potential in the treatment of disorders like those mentioned above. Of course, selectivity also reduces the potential for adverse effects mediated by other serotonin receptors.

INFORMATION DISCLOSURE

U.S. Pat. No. 3,253,989 discloses the use of mCPP as an anorectic agent.

EP-A1-863 136 discloses azetidine and pyrrolidine derivatives which are selective 5-$HT_{2C}$ receptor agonists having antidepressant activity and which can be used for treating or preventing serotonin-related diseases, including eating disorders and anxiety.

EP-A-657 426 discloses tricyclic pyrrole derivatives having activity on the 5-$HT_{2C}$ receptor and which inter alia may be used for treating eating disorders.

EP-A-655 440 discloses 1-aminoethylindoles having activity on the 5-$HT_{2C}$ receptor and which may be used for treating eating disorders.

EP-A-572 863 discloses pyrazinoindoles having activity on the 5-$HT_{2C}$ receptor and which may be used for treating eating disorders.

J. Med. Chem. 1978, 21, 536–542 and U.S. Pat. No. 4,081,542 disclose a series of piperazinylpyrazines having central serotonin-mimetic activity. In particular, U.S. Pat. No. 4,081,542 discloses such compounds as anorectic agents.

J. Med. Chem. 1981, 24, 93–101 discloses a series of piperazinylquinoxalines with central serotonin-mimetic activity.

WO 00/12475 discloses indoline derivatives as 5-$HT_{2B}$ and/or 5-$HT_{2C}$ receptor ligands, especially for the treatment of obesity.

WO 00/12510 discloses pyrroloindoles, pyridoindoles and azepinoindoles as 5-$HT_{2C}$ receptor agonists, particularly for the treatment of obesity.

WO 00/12482 discloses indazole derivatives as selective, directly active 5-$HT_{2C}$ receptor ligands, preferably 5-$HT_{2C}$ receptor agonists, particularly for use as anti-obesity agents.

WO 00/12502 discloses pyrroloquinolines as 5-$HT_{2C}$ receptor agonists, particularly for use as anti-obesity agents.

GB-B-1,457,005 discloses 1-piperazinyl-2-[2-(phenyl) ethenyl]-quinoxaline derivatives which exhibit anti-inflammatory activity.

Chem. Pharm. Bull. 1993, 41(10) 1832–1841 discloses 5-$HT_3$ antagonists including 2-(4-methyl-1-piperazinyl)-4-phenoxyquinoxaline.

GB-B-1,440,722 discloses 2-(1'-piperazinyl)-quinoxaline compounds having pharmaceutical activity against depression.

WO 96/11920 discloses CNS-active pyridinylurea derivatives.

WO 95/01976 discloses indoline derivatives active as 5-$HT_{2C}$ antagonists and of potential use in the treatment of CNS disorders.

WO 97/14689 discloses aryl-piperazine cyclic amine derivatives which are selective 5-$HT_{1D}$ receptor antagonists.

WO 98/42692 discloses piperazines derived from cyclic amines which are selective antagonists of human 5-$HT_{1A}$, 5-$HT_{1D}$ and 5-$HT_{1B}$ receptors.

GB-B-1,465,946 discloses substituted pyridazinyl, pyrimidinyl, pyrazinyl and pyridyl compounds which are active as β-receptor blocking agents.

EP-A-711757 discloses [3-(4-phenyl-piperazin-1-yl)propylamino]-pyridine, pyrimidine and benzene derivatives as α-adrenoceptor antagonists.

WO 99/03833 discloses aryl-piperazine derivatives which are 5-HT$_2$ antagonists and 5-HT$_{1A}$ receptor agonists and therefore are useful as remedies or preventives for psychoneurosis.

WO 96/02525 discloses aryl-piperazine-derived piperazide derivatives having 5-HT receptor antagonistic activity.

WO 99/58490 discloses aryl-hydronaphthalen-alkanamines which may effectuate partial or complete blockage of serotonergic 5-HT$_{2C}$ receptors in an organism.

WO 00/35922 discloses 2,3,4,4α-tetrahydro-1H-pyrazino[1,2-α]quinoxalin-5(6H)ones as 5-HT$_{2C}$ agonists, which may be used for the treatment of obesity.

WO 00/44737 discloses aminoalkylbenzofurans as 5-HT$_{2C}$ agonists, which may be used for the treatment of obesity.

Further compounds reported to be 5-HT$_{2C}$ receptor agonists are, for example, indazolylpropylamines of the type described in WO 00/12481; indazoles of the type described in WO 00/17170; piperazinylpyrazines of the type described in WO 00/76984, WO 02/40456 and WO 02/40457; heterocycle fused γ-carbolines of the type described in WO 00/77001, WO 00/77002 and WO 00/77010; benzofurylpiperazines of the type described in WO 01/09111 and WO 01/09123; benzofurans of the type described in WO 01/09122; benzothiophenes of the type described in 01/09126; aminoalkylindazoles of the type described in WO 98/30548; indoles of the type described in WO 01/12603; indolines of the type described in WO 01/12602 and WO 02/44152; pyrazino(aza)indoles of the type described in WO 00/44753; diaza-cyclopenta[α]indenes of the type described in EP 1132389; piperazine derivatives of the type described in WO 02/10169; quinoxalinones of the type described in U.S. Pat. No. 6,372,745, and tricyclic pyrroles or pyrazoles of the type described in WO 98/56768.

WO 98/33504 discloses a new medical use of 1-[6-chloro-5-(trifluoromethyl)-2-pyridinyl]piperazine, in particular to a new method of treating urinary incontinence.

WO 02/36596 discloses cycloalkyl[b][1,4]-diazepino[6,7-hi]indoles as serotonin 5-HT$_{2C}$ receptor agonists, which may be used for the treatment of obesity.

WO 03/00666 discloses [1,2']bipyrazinyl 5-HT$_2$ receptor ligands, in particular 5-HT$_{2c}$ receptor ligands, for treatment of sexual dysfunction.

WO 03/00663 discloses piperazinylpyrimidines as 5-HT$_2$ receptor ligands, in particular 5-HT$_{2c}$ receptor ligands, for treatment of sexual disorders.

WO 02/51844 discloses cycloalkyl fused indole derivatives and their use as 5-HT$_{2b}$ and 5-HT$_{2c}$ receptor ligands.

WO 02/42304 discloses cyclopenta[b][1,4]diazepino[6,7,1-hi]indoles as selective 5-HT$_{2c}$ receptor agonists.

WO 02/36596 discloses diazepinocarbazoles and related compounds as serotonin 5-HT$_{2c}$ agonists.

WO 02/48124 discloses piperazine derivatives as 5-HT$_{2c}$ receptor agonists, which may be used for, e.g., obesity.

WO 01/66548 discloses azaindolyl derivatives as 5-HT$_{2b}$ and 5-HT$_{2c}$ receptor ligands, preferably 5-HT$_{2c}$ receptor agonists, for use in therapy, especially for use as anti-obesity agents.

WO 02/072584 discloses tetrahydropyrazinoindoles as 5-HT$_{2b}$ and 5-HT$_{2c}$ receptor ligands, preferably 5-HT$_{2c}$ receptor agonists, for use in therapy, especially for use as anti-obesity agents.

WO 00/76984 and WO 02/40457 disclose aryl-piperazine derivatives which bind to the 5-HT$_{2C}$ receptor (agonists and antagonists) useful for the treatment of serotonin-related disorders. However, the 5-HT$_{2C}$ receptor selectivity of the compounds according to the present invention is unexpectedly high compared to the compounds according to WO 00/76984 and WO 02/40457.

The absence of appreciable affinity to certain other 5-HT receptor subtypes may provide the basis for an improved therapeutic index compared with the general activation of all the different 5-HT receptor subtypes by 5-HT reuptake inhibitors and/or 5-HT releasing agents. The anti-obesity drug dexfenfluramine, a 5-HT reuptake inhibitor and 5-HT releaser, was withdrawn from the market in September 1997 because of several reports suggesting the association of this drug with a risk of primary pulmonary hypertension and of heart valve abnormalities (see, e.g. Kolanowski, J. A risk-benefit assessment of anti-obesity drugs. Drug Safety 1999, 20, 119–131). The 5-HT/noradrenaline reuptake inhibitor sibutramine, currently on the market for the treatment of obesity, can increase blood pressure and heart rate in some patients. The use of sibutramine has been suspended in Italy in March 2002 because of two cardiovascular deaths and its safety is currently under review in other European countries where, in the UK and France alone, there have been a total of 103 serious adverse reaction reports in people using the drug including two deaths in Britain. Taken together, there is a need for the development of safer anti-obesity agents.

It is important to minimize potential adverse advents due to activation of 5-HT$_{2A}$ and 5-HT$_{2B}$ receptor subtypes. 5-HT$_{2A}$ receptor agonism is associated with vasoconstriction, platelet aggregation and hallucinogenic episodes and 5-HT$_{2B}$ receptor agonism might play a role in the pathophysiology of migraine. Stimulation of 5-HT$_{2A}$ and 5-HT$_{2B}$ receptors might also have a link to cardiac fibrosis.

The following references show that hallucinogenic effects are associated with activation of the 5-HT$_{2A}$ receptor:

(a) Glennon, R. A. et al. Hallucinogens and Serotonergic Mechanisms. NIDA Res. Mongr. 1992, 119P, 131–135.
(b) Egan, C. T. et al. Agonist Activity of LSD and Lisuride at cloned 5-HT$_{2A}$ and 5-HT$_{2C}$ receptors. Psychopharmacol. 1998, 136, 409–414.
(c) Roth, B. L. et al. The multiplicity of serotonin receptors: Uselessly diverse molecules or an embarrassment of riches? Neuroscientist 2000, 6, 252–262.
(d) Arvanov, V. L. et al. LSD and DOB: interaction with 5-HT$_{2A}$ receptors to inhibit NMDA receptor-mediated transmission in the rat prefrontal cortex. Eur. J. Neurosci. 1999, 11, 3064-3072.
(e) Marek, G. J. et al. LSD and the phenethylamine hallucinogen DOI are potent partial agonists at 5-HT$_{2A}$ receptors on interneurons in rat piriform cortex. J. Pharmacol. Exp. Ther. 1996, 278, 1373–1382.
(f) Roth, B. L. et al. Activation is hallucinogenic and antagonism is therapeutic: role of 5-HT$_{2A}$ receptors in atypical antipsychotic drug actions. Neuroscientist 1999, 5, 254–262.
(g) Aghajanian, G. K. et al. Serotonin and Hallucinogens. Neuropsychopharmacology 1999, 21, 16S-23S.
(h) Aghajanian, G. K. et al. Serotonin model of schizophrenia: emerging role of glutamate mechanisms. Brain Res. Rev. 2000, 31, 302–312.

The following references show that vasoconstrictive effects are associated with activation of the 5-HT$_{2A}$ receptor:

(a) Roth, B. L. et al. 5-HT2-family receptors (5-HT$_{2A}$, 5-HT$_{2B}$, 5-HT$_{2C}$): where structure meets function. Pharmacol. Ther. 1998, 79, 231–257.

(b) Florian, J. A. et al. Integration of mitogen-activated protein kinase activation in vascular 5-hydroxytryptamine 2A receptor signal transduction. J. Pharmacol. Exp. Ther. 1998, 284, 346-355.

(c) Saxena, P. R. Serotonin receptors: Subtypes, functional responses and therapeutic relevance. Pharmacol. Ther. 1995, 66, 339–368.

(d) MacLennan, S. J. 5-HT receptors in the human cardiovascular system. ID Res. Alert 1997, 2, 207–213.

(e) Nilsson, T. et al. Characterisation of 5-HT receptors in human coronary arteries by molecular and pharmacological techniques. Eur. J. Pharmacol. 1999, 372, 49–56.

(f) MacLean, M. R. et al. 5-Hydroxytryptamine receptors mediating vasoconstriction in pulmonary arteries from control and pulmonary hypertensive rats. Br. J. Pharmacol. 1996, 119, 917–930.

(g) Cortijo, J. et al. Characterization of 5-HT receptors on human pulmonary artery and vein: functional and binding studies. Br. J. Pharmacol. 1997, 122, 1455–1463.

(h) O'Connor, S. E. et al. Cardiovascular effects of SL65.0472, a 5-HT receptor antagonist. Eur. J. Pharmacol. 2001, 414, 259–269.

(i) Galzin, A.-M. et al. Effects of SL 65.0472, a novel 5-HT receptor antagonist, on 5-HT receptor mediated vascular contraction. Eur. J. Pharmacol. 2000, 404, 361–368.

The following references show that $5\text{-}HT_{2A}$ agonism is associated with platelet aggregation, thrombosis and atherosclerosis:

(a) Li, N. et al. Effects of serotonin on platelet activation in whole blood. Blood Coagul Fibrinolysis 1997, 8, 517–523.

(b) Takano, S. Role of 5-hydroxytryptamine in platelet thrombus formation and mechanisms of inhibition of thrombus formation by 5-hydroxytryptamine 2A antagonists in rabbits. Arch. Int. Pharmacodyn. Ther. 1995, 330, 297–308.

(c) de Clerck, F. The role of serotonin in thrombogenesis. Clin. Physiol. Biochem. 1990, 8 (Suppl. 3), 40–49.

One of the initiating events of atherosclerois is endothelial injury followed by platelet aggregation. During atherosclerosis, platelets aggregate more readily and greater quantities of serotonin are released from platelets. Vascular responses to serotonin released by activated platelets are profoundly altered in a direction that favours vasoconstriction (arterial spasm), which ultimately may lead to thrombosis and complete obstruction of the vessel. Vascular smooth muscle cell proliferation is believed to play an important role in the pathogenesis of atherosclerosis. Serotonin is known to be a mitogen for vascular smooth muscle cells by stimulation of the $5\text{-}HT_{2A}$ receptor [tentatively via activation of MAPK (mitogen-activated protein kinase) and/or PKC (protein kinase C) dependent pathways], see:

(a) Lee, S.-L. et al. Serotonin stimulates mitogen-activated protein kinase activity through the formation of superoxide anion. Am. J. Physiol. 1999, 277, (2Pt.1), L-282-L291.

(b) Florian, J. A. et al. Integration of mitogen-activated protein kinase activation in vascular 5-hydroxytryptamine$_{2A}$ receptor signal transduction. J. Pharmacol. Exp. Ther. 1998, 284, 346–355.

(c) Banes A. et al. Mechanisms of 5-hydroxytryptamine$_{2A}$ receptor activation of the mitogen-activated protein kinase pathway in vascular smooth muscle. J. Pharmacol. Exp. Ther. 1999, 291, 1179–1187.

(d) Watanabe, T. et al. Lipid peroxidation product 4-hydroxy-2-nonenal acts synergistically with serotonin in inducing vascular smooth muscle cell proliferation. Atherosclerosis 2001, 155, 37–44.

(e) Pakala, R. et al. Eicosapentaenoic Acid and Docosahexaenoic Acid Block Serotonin-Induced Smooth Muscle Cell Proliferation. Atherioscler. Thromb. Vasc. Biol. 1999, 19, 2316–2322.

Furthermore, it has been suggested that increased vasoconstrictor response to 5-HT in atherosclerotic vessels might be due to supersensitive $5\text{-}HT_{2A}$ receptors, see: Fujiwara, T. et al. Augmented responses to $5\text{-}HT_2$-receptor-mediated vasoconstrictions in atherosclerotic rabbit common carotid arteries. J. Cardiovase. Pharmacol. 1995, 26, 503–510.

A 5-HT-induced upregulation of thrombin receptor expression in vascular smooth muscle cells, via activation of $5\text{-}HT_{2A}$ receptors, has also been implicated to play a role in atherosclerosis, see: Schini-Kerth V. B. et al. Serotonin stimulates the expression of thrombin receptors in cultured vascular smooth muscle cells. Role of protein kinase C and protein tyrosine kinases. Circulation 1996, 93, 2170–2177.

The following references show that $5\text{-}HT_{2B}$ agonism is associated with migraine:

(a) Schmuck, K. et al. Activation of meningeal $5\text{-}HT_{2B}$ receptors: an early step in the generation of migraine headache. Eur. J. Neurosci. 1996, 8, 959–967.

(b) Johnson, K. W. et al. Serotonin in migraine: Theories, animal models and emerging therapies. Prog. Drug. Res. 1998, 51, 219–244.

(c) Parsons, A. A. Prophylaxis of migraine. Curr. Opin. CPNS Invest. Drugs 2000, 2, 160–166.

The following reference show that pulmonary hypertension is associated with activation of the $5\text{-}HT_{2B}$ receptor:

(a) Launay, J.-M. et al. Function of the serotonin 5-hydroxytryptamine 2B receptor in pulmonary hypertension. Nature Med. 2002, 8, 1129–1135.

The following references show that $5\text{-}HT_{2A}$ and especially $5\text{-}HT_{2B}$ agonism is associated with the origin of cardiac fibrosis after treatment with marketed anti-obesity preparations such as dexfenfluramin:

(a) Rothman, R. B. et al. Evidence for possible involvment of $5\text{-}HT_{2B}$ receptors in the cardiac valvulopathy associated with fenfluramine and other serotonergic medications. Circulation 2000, 102, 2836–2841.

(b) Fitzgerald, L. W. et al. Possible role of valvular serotonin $5\text{-}HT_{2B}$ receptors in the cardiopathy associated with fenfluramine. Mol. Pharmacol. 2000, 57, 75–81.

(c) Setola, V. et al. 3,4-Methylenedioxymethamphetamine (MDMA, "Ecstasy") induces fenfluramine-like proliferative actions on human cardiac valvular interstitial cells in vitro. Mol. Pharmacol. 2003, 63, 1223–1229.

As denoted below, the present compounds may be used in order to treat serotonin-related conditions such as menopausal and post-menopausal hot flushes. Berendsen H. H. G. "Hot flushes and serotonin". Journal of the British Menopause Society. 2002, 8, 30–34, indicates that non-hormonal treatment with either $5\text{-}HT_{2A}$ receptor antagonists or $5\text{-}HT_{2C}$ receptor agonists may have several advantages over hormonal therapy.

Another example of serotonin-related disorders is weight gain associated with antipsychotic drug administration. WO 02/19998 discloses that the use of atypical antipsychotic agents is associated with weight gain in up to 50% of patients, a significant portion of the patient population. Piesla, M. J. et al. Atypical antipsychotic-like effects of $5\text{-}HT_{2C}$ agonists. Schizophrenia Res. 2001, 49 (1–2; Sp Iss, Suppl.) 95, discloses that $5\text{-}HT_{2C}$ agonists have anti-psychotic potential. Therefore, therapy using $5\text{-}HT_{2C}$ agonists will probably counteract an increase in body weight induced by antipsychotic drugs without counteracting the antipsychotic effect. It is reasonable to expect that the antipsychotic effect will be strengthened.

SUMMARY OF THE INVENTION

According to the present invention, a class of novel compounds have been developed which bind to the 5-$HT_{2C}$ receptor, which compounds may be agonists, partial agonists or antagonists for this receptor, preferably agonists or partial agonists. Therefore, the present compounds may be used for the treatment of serotonin-related disorders and conditions. Furthermore, it has been shown that the 5-$HT_{2C}$ receptor selectivity of the present compounds is unexpectedly high compared to prior art compounds.

In one aspect, the invention provides novel compounds of the general Formula (I):

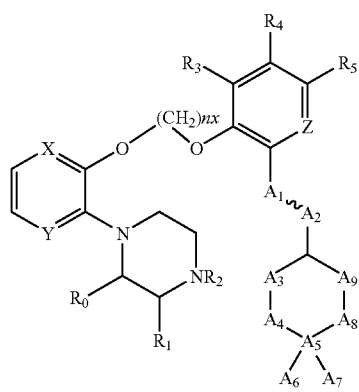

Formula (I)

wherein
nx is 2–4, preferably 2;
$R_0$ and $R_1$ are each independently H or $CH_3$;
$R_2$ is H, $C_1$–$C_4$-alkyl, 2-hydroxyethyl, 2-cyanoethyl or tetrahydropyran-2-yl, $C_1$–$C_4$-acyl or $C_1$–$C_4$-alkoxycarbonyl;
$R_3$–$R_5$ are each independently H, halogen, methyl or methoxy, provided that at least one of $R_3$–$R_5$ is hydrogen;
X, Y, and Z are each independently CH or N;
$A_1$ is O, CH or $CH_2$;
$A_2$ is O, CH or $(CH_2)_{n2}$, wherein n2 is an integer 0–2;
the bond between $A_1$ and $A_2$ is a single or double bond;
$A_3$ is $(CH_2)_{n3}$, wherein n3 an integer 0–10, preferably 0–7, more preferably 0–5;
$A_4$ is $(CMe_2)_{n4}$, wherein n4 is an integer 0–1;
$A_5$ is N or O;
$A_6$ and $A_7$ are each independently H, $C_1$–$C_4$-alkyl, amino-$C_2$–$C_4$-alkyl, N,N-di-$C_1$–$C_4$-alkylamino-$C_2$–$C_4$-alkyl, $C_3$–$C_6$-cycloalkyl or form together with $A_5$ a saturated heterocyclic ring;
$A_8$ is $(CH_2)_{n8}$, wherein n8 is an integer 0–2;
$A_9$ is H or $CH_2$;
or pharmaceutically acceptable salts, solvates, hydrates, geometrical isomers, tautomers, optical isomers, N-oxides and prodrug forms thereof;
provided that when $A_5$ is N, then $A_5$ is substituted by only two of $A_6$, $A_7$ and $A_8$; when $A_5$ is O, then $A_5$ is substituted by only one of $A_6$, $A_7$ and $A_8$.

In case the compounds of Formula (I) can be in the form of optical isomers, the invention comprises the racemic mixture as well as the individual enantiomers as such.

In other aspects, the compounds of formulae (I) are those wherein:

In case at least one of the integers n2, n3, n4 or n8 referred to above equals 0, then the corresponding group $A_2$, $A_3$, $A_4$ or $A_8$ equals a single bond. However, in the case when $A_9$ equals H, then $A_8$ does not equal a single bond between $A_5$ and $A_9$. In the case when n8 equals 1 or 2, then $A_5$ is not substituted by $A_7$.

When $A_1$ is $CH_2$, $A_2$ is O and $A_5$ is N, then both n3 and n4 are not 0.

When one of $A_1$ and $A_2$ is O, the other of $A_1$ and $A_2$ may not be O.

When one of $A_1$ and $A_2$ is CH, then the other of $A_1$ and $A_2$ is also CH, wherein the bond between $A_1$ and $A_2$ is a double bond.

When $A_5$ is O, then $A_5$ is not substituted by $A_7$ and $A_8$, and $A_9$ represents H and $A_6$ is amino-$C_2$–$C_4$-alkyl or N,N-di-$C_1$–$C_4$-alkylamino-$C_2$–$C_4$-alkyl, and further n3 and n4 are preferably both 0.

When $A_3$, $A_4$, $A_5$, $A_8$ and $A_9$ together with the carbon atom between $A_3$ and $A_9$ form a 4–7 membered saturated heterocyclic ring (e.g. azacyclic ring), then $A_9$ is $CH_2$, n4 is 0, and the sum of n3+n8 is an integer 1–4.

When $A_9$ is $CH_2$, then all of n3, n4, and n8 are not 0.

When $A_9$ is $CH_2$ and $A_5$ is N, then n4 is 0. When n4 is 1, then $A_9$ is preferably H and $A_5$ is preferably N.

When $A_5$ is nitrogen, the $A_6$ and $A_7$ are each independently H, $C_1$–$C_4$-alkyl, $C_3$–$C_6$-cycloalkyl or form together a saturated heterocyclic ring.

In case $R_0$ is methyl, it is preferred that the carbon atom, to which the said methyl group $R_0$ is attached, is in the (R)-configuration.

It is preferred that $R_1$ is hydrogen.
It is also preferred that X and Y both are nitrogen.
It is also preferred that $R_2$ is H or methyl.
It is also preferred that all of $R_3$–$R_5$ are H.
It is also preferred that $A_6$ and $A_7$ are each independently H, methyl, isopropyl, 2-ethylamine or form together with $A_5$ a pyrrolidine or piperazine ring.

In one preferred embodiment, the invention refers to a compound of Formula (Ia):

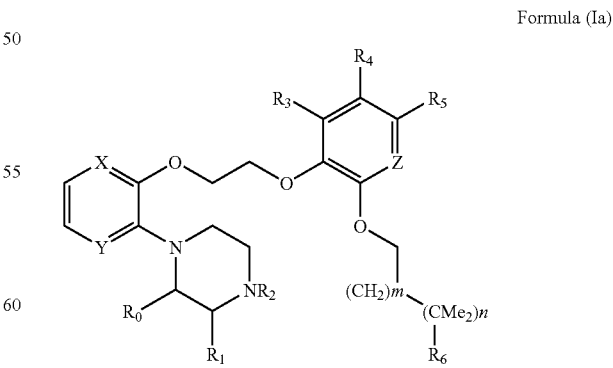

Formula (Ia)

wherein:
$R_0$–$R_5$, X, Y, and Z are as defined above, preferably wherein Z is N, m is an integer 0–10, preferably 0–7, more preferably 0–5,
n is an integer 0 or 1, wherein the sum of m+n is preferably at least 1, $R_6$ is $NR_7R_8$ or $OR_9$, wherein $R_7$ and $R_8$ are each independently H or straight or branched $C_1$–$C_4$-alkyl;

or $R_7$ and $R_8$ form together with the nitrogen atom to which they are attached a saturated heterocyclic ring;

$R_9$ is amino-$C_2$–$C_4$-alkyl or N,N-di-$C_1$–$C_4$-alkylamino-$C_2$–$C_4$-alkyl.

It is preferred that $R_7$ and $R_8$ are selected from H, methyl, isopropyl, or form together with the nitrogen atom to which they are attached a pyrrolidine or piperazine ring. It is also preferred that $R_9$ is 2-aminoethyl.

Specific compounds of Formula (Ia) are:

N,N-Dimethyl-(2-(3-[2-(2-(R)-methyl-3,4,5,6-tetrahydro-2H-[1,2']bipyrazinyl-3'-yloxy)-ethoxy]-pyridin-2-yloxy)-ethyl)-amine;

N,N-Diisopropyl-(2-(3-[2-(2-(R)-methyl-3,4,5,6-tetrahydro-2H-[1,2']bipyrazinyl-3'-yloxy)-ethoxy]-pyridin-2-yloxy)-ethyl)-amine;

N,N-Dimethyl-2-[(3-{2-[(3-piperazin-1-ylpyrazin-2-yl)oxy]ethoxy}pyridin-2-yl)oxy]ethanamine;

2-[(2R)-2-Methylpiperazin-1-yl]-3-(2-{[2-(2-pyrrolidin-1-ylethoxy)pyridin-3-yl]oxy}ethoxy)pyrazine;

N,N-Dimethyl-4-({3-[2-({3-[(2R)-2-methylpiperazin-1-yl]pyrazin-2-yl}oxy)ethoxy]pyridin-2-yl}oxy)butan-1-amine;

N-Methyl-N-[2-({3-[2-({3-[(2R)-2-methylpiperazin-1-yl]pyrazin-2-yl}oxy)ethoxy]pyridin-2-yl}oxy)ethyl]propan-2-amine;

N,N-Dimethyl-3-({3-[2-({3-[(2R)-2-methylpiperazin-1-yl]pyrazin-2-yl}oxy)ethoxy]pyridin-2-yl}oxy)propan-1-amine;

N,N,2-Trimethyl-1-({3-[2-({3-[(2R)-2-methylpiperazin-1-yl]pyrazin-2-yl}oxy)ethoxy]pyridin-2-yl}oxy)propan-2-amine;

[2-({3-[2-({3-[(2R)-2-Methylpiperazin-1-yl]pyrazin-2-yl}oxy)ethoxy]pyridin-2-yl}oxy)ethyl]amine;

N-Methyl-2-({3-[2-({3-[(2R)-2-methylpiperazin-1-yl]pyrazin-2-yl}oxy)ethoxy]pyridin-2-yl}oxy)ethanamine;

2-{2-[{2-[2-(Dimethylamino)ethoxy]pyridin-3-yl}oxy]ethoxy}-3-[(2R)-2,4-dimethylpiperazin-1-yl]pyrazine;

2-[2-(2-[2-(Dimethylamino)ethoxy]phenoxy)ethoxy]-3-[(2R)-2-methylpiperazin-1-yl]pyrazine;

{2-[2-({3-[2-({3-[(2R)-2-Methylpiperazin-1-yl]pyrazin-2-yl}oxy)ethoxy]pyridin-2-yl}oxy)ethoxy]ethyl}amine;

[6-({3-[2-({3-[(2R)-2-Methylpiperazin-1-yl]pyrazin-2-yl}oxy)ethoxy]pyridin-2-yl}oxy)hexyl]amine;

[5-({3-[2-({3-[(2R)-2-Methylpiperazin-1-yl]pyrazin-2-yl}oxy)ethoxy]pyridin-2-yl}oxy)pentyl]amine 5-({3-[2-({3-[(2R)-2,4-Dimethylpiperazin-1-yl]pyrazin-2-yl}oxy)ethoxy]pyridin-2-yl}oxy)-N,N-dimethylpentan-1-amine;

2-[(2R)-2-Methylpiperazin-1-yl]-3-(2{[2-(2-piperazin-1-ylethoxy)pyridin-3-yl]oxy}ethoxy)pyrazine.

In another preferred embodiment, the invention refers to a compound of Formula (Ib):

Formula (Ib)

wherein:
$R_0$–$R_5$, X, Y, and Z are as defined above,
o is an integer 0–2;
p is an integer 0–2, wherein o and p are preferably not both 0;
q is an integer 0–1;
$R_{10}$ is H or $C_1$–$C_4$-alkyl, preferably H or methyl.

Specific compounds of Formula (Ib) are:

2-[(2R)-2-Methylpiperazin-1-yl]-3-[2-({2-[(1-methylpiperidin-4-yl)oxy]pyridin-3-yl}oxy)ethoxy]pyrazine;

2-[(2R)-2-Methylpiperazin-1-yl]-3-[2-({2-[2-(1-methylpyrrolidin-2-yl)ethoxy]pyrazine-3-yl}oxy)ethoxy]pyrazine:

2-[(2R)-2-Methylpiperazin-1-yl]-3-(2-{[2-(piperidin-3-ylmethoxy)pyridin-3-yl]oxy}ethoxy)pyrazine;

2-[(2R)-2-Methylpiperazin-1-yl]-3-{2-[(2-{[(2S)-1-methylpyrrolidin-2-yl]methoxy}pyridin-3-yl)oxy]ethoxy}pyrazine.

In another preferred embodiment, the invention refers to a compound of Formula (Ic):

Formula (Ic)

wherein:
$R_0$–$R_5$, X, Y, and Z are as defined above,
t is an integer 1–11, preferably 1–8, more preferably 1–6, most preferably 1,
the orientation around the double bond may be either cis or trans;

$R_{11}$ and $R_{12}$ are each independently H or straight or branched $C_1$–$C_4$-alkyl;

or $R_{11}$ and $R_{12}$ form together with the nitrogen atom to which they are attached a saturated heterocyclic ring.

It is preferred that $R_{11}$ and $R_{12}$ are both methyl.

Specific compounds of Formula (Ic) are:

2-{2-[{2-[(1Z)-3-(Dimethylamino)prop-1-enyl]pyridin-3-yl}oxy]ethoxy}-3-[(2R)-2-methylpiperazin-1-yl]pyrazine;

2-{2-[{2-[(1-E)-3-(Dimethylamino)prop-1-enyl]pyridin-3-yl}oxy]ethoxy}-3-[(2R)-2-methylpiperazin-1-yl]pyrazine.

In another preferred embodiment, the invention refers to a compound of Formula (Id)

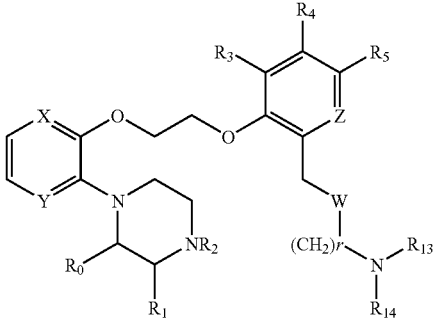

Formula (Id)

wherein:

$R_0$–$R_5$, X, Y, and Z are as defined above,

W is O or $CH_2$;

r is 1–11, preferably 1–8, more preferably 1–6, most preferably 1 when W is $CH_2$ and most preferably 2 when W is O;

$R_{13}$ and $R_{14}$ are each independently H or straight or branched $C_1$–$C_4$-alkyl;

or $R_{13}$ and $R_{14}$ form together with the nitrogen atom to which they are attached a saturated heterocyclic ring.

In case W is O, then it is preferred that X=N and Y=N. In case W is $CH_2$, then it is preferred that r=t, X=N, Y=N, $R_{13}$=$R_{11}$ and $R_{14}$=$R_{12}$, where t, $R_{11}$ and $R_{12}$ are as defined in formula (Ic).

It is preferred that $R_{13}$ and $R_{14}$ are both methyl.

Specific compounds of Formula (Id) are:

2-{2-[(2-{[2-(Dimethylamino)ethoxy]methyl}pyridin-3-yl)oxy]ethoxy}-3-[(2R)-2-methylpiperazin-1-yl]pyrazine;

2-{2-[{2-[3-(Dimethylamino)propyl]pyridin-3-yl}oxy]ethoxy}-3-[(2R)-2-methylpiperazine-1-yl]pyrazine.

The compounds of each of Formula (I), (Ia), (Ib), (Ic) and (Id) are collectively referred to as those of Formulae (I).

In case the compounds of Formulae (I) contain groups which may exist in tautomeric forms, the invention comprises the tautomeric forms of the compounds as well as mixtures thereof.

In case the compounds of Formulae (I) can be in the form of geometrical isomers, the invention comprises the geometrical isomers as well as mixtures thereof.

In another aspect, the invention provides the compounds according to Formulae (I) above for use in therapy of a human being or an animal.

Still another aspect of the invention provides a pharmaceutical composition comprising a compound according to Formulae (I) above as the active ingredient, preferably together with a pharmaceutically acceptable carrier and, if desired, other pharmacologically active agents.

In yet another aspect, the invention provides a method for the treatment of a human or animal subject suffering from a serotonin-related disorder or condition, particularly 5-$HT_{2C}$ receptor-related, such as memory disorders, such as Alzheimer's disease; schizophrenia; mood disorders such as depression; anxiety disorders; pain; substance abuse; sexual dysfunctions such as erectile dysfunction; epilepsy; glaucoma; urinary disorders, such as urinary incontinence; menopausal and post-menopausal hot flushes; type 2 diabetes; eating disorders, such as binge eating disorders, anorexia nervosa and bulimia; weight gain associated with antipsychotic drug administration, premenstrual tension, sleep disorders; and particularly obesity.

Another aspect of the invention provides the use of the compounds according to Formulae (I) above for the manufacture of a medicament for the treatment of a serotonin-related disorder or condition, particularly 5-$HT_{2C}$ receptor-related, such as memory disorders, such as Alzheimer's disease; schizophrenia; mood disorders such as depression; anxiety disorders; pain; substance abuse; sexual dysfunctions such as erectile dysfunction; epilepsy; glaucoma; urinary disorders, such as urinary incontinence; menopausal and post-menopausal hot flushes; type 2 diabetes; eating disorders, such as binge eating disorders, anorexia nervosa and bulimia; weight gain associated with antipsychotic drug administration, premenstrual tension, sleep disorders; and particularly obesity. The method can include administering to a subject (e.g., a human or an animal) in need thereof an effective amount of one or more compounds of Formulae (I), their salts, or compositions containing the compounds or salts.

Another aspect of the invention provides methods for modulating 5-$HT_{2C}$ receptor function comprising contacting the receptor with an effective stimulatory or inhibitory amount of a compound according to Formulae (I) above, preferably an effective stimulatory amount thereof.

The methods delineated herein can also include the step of identifying that the subject is in need of treatment of the serotonin-related disorder or condition. Identifying a subject in need of such treatment can be in the judgment of a subject or a health care professional and can be subjective (e.g., opinion) or objective (e.g., measurable by a test or diagnostic method).

This invention also features a method for preparing a composition. The method includes combining a compound of Formulae (I) with a pharmaceutically acceptable carrier.

Still another aspect of the invention provides methods for the preparation of the compounds according to Formulae (I) above.

A further aspect of the invention relates to a method for treating a disorder or condition, comprising administering to a subject in need thereof an effective amount of a compound of Formulae (I) above, wherein the disorder or condition is selected from memory disorders including Alzheimer's disease; schizophrenia; mood disorders such as depression; anxiety disorders; pain; substance abuse; sexual dysfunctions such as erectile dysfunction; epilepsy; glaucoma; urinary disorders, such as urinary incontinence; menopausal and post-menopausal hot flushes; type 2 diabetes; eating disorders, such as binge eating disorders, anorexia nervosa and bulimia; weight gain associated with antipsychotic drug administration, premenstrual tension, sleep disorders; and particularly obesity.

A still further aspect of the invention relates to the use of the compounds of Formulae (I) above for the manufacture of a medicament for the treatment of memory disorders including Alzheimer's disease; schizophrenia; mood disorders such as depression; anxiety disorders; pain; substance abuse; sexual dysfunctions such as erectile dysfunction; epilepsy; glaucoma; urinary disorders, such as urinary incontinence;

menopausal and post-menopausal hot flushes; type 2 diabetes; eating disorders, such as binge eating disorders, anorexia nervosa and bulimia; weight gain associated with antipsychotic drug administration, premenstrual tension, sleep disorders; and particularly obesity.

DETAILED DESCRIPTION OF THE INVENTION

First, the various terms used, separately and in combinations, in the above definition of the compounds having the general Formula (I) (and each of Formulae (I))will be explained.

$C_1$–$C_4$-alkyl, which may be straight or branched, is an alkyl group having 1–4 carbon atoms. Exemplary alkyl groups include methyl, ethyl, n-propyl, isopropyl, n-butyl, sec-butyl, isobutyl, and tert-butyl.

Amino-$C_2$–$C_4$-alkyl, which may be straight or branched, is a $C_2$–$C_4$-alkyl group directly attached to an amino group. Exemplary aminoalkyl groups include 2-aminoethyl, 3-amino-n-propyl, and 4-amino-n-butyl.

$C_3$–$C_6$-cycloalkyl is a cyclic alkyl group having 3–6 carbon atoms. Exemplary cycloalkyl groups are cyclopropyl, cyclobutyl, cyclopentyl, and cyclohexyl.

$C_1$–$C_4$-acyl, which may be straight or branched, is an acyl group having 1–4 carbon atoms. Exemplary acyl groups include formyl, acetyl, propionyl, n-butyryl, and isobutyryl.

$C_1$–$C_4$-alkoxy, which may be straight or branched, is an alkoxy group having 1–4 carbon atoms. Exemplary alkoxy groups include methoxy, ethoxy, n-propoxy, isopropoxy, n-butoxy, sec-butoxy, isobutoxy, and tert-butoxy.

$C_1$–$C_4$-alkoxycarbonyl means a $C_1$–$C_4$-alkoxy group directly connected to a carbonyl group. An exemplary alkoxycarbonyl group is tert-butoxycarbonyl (t-BOC).

DCM means dichloromethane, DMSO means dimethylsulfoxide, halogen means fluoro, chloro, bromo, or iodo, HOAc means acetic acid, HPLC means high performance liquid chromatography, HRMS means high resolution mass spectrometry, "OTs" means tosylate i.e. para-toluenesulfonate, "OMs" means mesylate i.e. methanesulfonate, TEA means triethylamine, TFA means trifluoroacetic acid, THF means tetrahydrofuran.

The term "saturated heterocyclic" refers to a heterocyclic ring that is non-aromatic (e.g., partially or fully saturated) and that has carbon atoms and one or two heteroatoms selected from O, S, and N (preferably from O and N and more preferably from N). Examples of saturated heterocyclic rings have 4–7 members and include piperidine, azetidine, morpholine, thiomorpholine, pyrrolidine, and piperazine.

Hydrogenation catalyst means a catalyst suitable for catalytic hydrogenation ordebenzylation. Examples of hydrogenation catalysts are palladium on carbon (Pd/C), Raney-Nickel, platinum, platinum oxide and zinc oxide.

Hydrogen source means a reagent used to introduce a hydrogen atom on any atom of a compound, including a carbon or oxygen atom. Examples of hydrogen sources are hydrogen gas and ammonium formate.

Hydroxyethylating agent means a reagent used to introduce a hydroxyethyl group on an oxygen or nitrogen atom of a compound. Examples of hydroxyethylating agents are ethylene carbonate, 2-bromoethanol, 2-chloroethanol and ethylene oxide.

For the transformation of an alcohol function into an aldehyde function, the method by Swern et al., J. Org. Chem. 1978, 43, 2480–2482, may be used. According to this method, the alcohol is reacted with dimethyl sulfoxide and oxalyl chloride in dichloromethane at a temperature of −78° C.

For the transformation of an alcohol function into a suitable leaving group, one may treat the alcohol with methanesulfonic anhydride in the presence of triethylamine in dichloromethane at a temperature of 0° C., e.g. as disclosed in J. Org. Chem. 2000, 65, 7839–7846.

A base is any substance that produces a negative ion and denotes electrons to an acid, if present. The term "base" as used herein, represents a reagent capable of accepting protons during the course of a reaction. Examples of bases include carbonate salts such as potassium carbonate, potassium bicarbonate, sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, and potassium hydroxide; alkoxides such as sodium tert-butoxide, potassium tert-butoxide, and lithium tert-butoxide; alkylamines such as triethylamine, diisopropylamine, and diisopropylethylamine; heterocyclic amines such as 4-dimethylaminopyridine, 2,6-lutidine, 1-methylimidazole, pyridine; bicyclic amines such as 1,8-diazabicyclo(4.3.0)undec-7-ene; and hydrides such as lithium hydride, sodium hydride, and potassium hydride. The base chosen for a particular conversion depends on the nature of the starting materials, the solvent or solvents in which the reaction is conducted, and the temperature at which the reaction is conducted.

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, 8th ed., McGraw-Hill, Int. Ed. 1992, "Biotransformation of Drugs, p. 13–15; and "The Organic Chemistry of Drug Design and Drug Action" by Richard B. Silverman. Chapter 8, p 352. (Academic Press, Inc. 1992. ISBN 0-12-643730-0).

"Pharmaceutically acceptable" means being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, malic acid, oxalic acid, toluenesulphonic acid, methanesulphonic acid, trifluoroacetic acid, fumaric acid, succinic acid, tartaric acid, citric acid, benzoic acid, ascorbic acid, isethionic acid (i.e. 2-hydroxyethylsulphonic acid) and the like.

"Treatment" as used herein includes prophylaxis of the named disorder or condition, or amelioration or elimination of the disorder or condition once it has been established.

It should be noted that both E- and Z-isomers of the compounds, optical isomers, as well as mixtures thereof, and all isotopes are included within the scope of the invention. E means "entgegen" (trans-isomer) and Z means "zusammen" (cis-isomer).

Presently preferred compounds of the general Formula (I) above are the compounds according to Examples 1–3 and 6–27; and their pharmacologically acceptable salts and solvates.

As mentioned above, the compounds of the present invention are useful for the treatment of a human or animal subject suffering from a serotonin-related disorder or condition, particularly 5-HT$_{2C}$ receptor-related, such as memory disorders, such as Alzheimer's disease; schizophrenia; mood disorders such as depression; anxiety disorders; pain; substance abuse; sexual dysfunctions such as erectile dysfunction; epilepsy; glaucoma; urinary disorders, such as urinary incontinence; menopausal and post-menopausal hot flushes; type 2 diabetes; eating disorders, such as binge eating disorders, anorexia nervosa and bulimia; weight gain associated with antipsychotic drug administration, premenstrual tension, sleep disorders; and particularly obesity. The 5-HT$_{2C}$ receptor-related disorder includes any disorder or condition that is modulated by the 5-HT$_{2C}$ receptor. Preferably, the compounds of the present invention may be used in the treatment of disorders and conditions where a 5-HT$_{2C}$ receptor agonist is desired or required.

The compounds of the present invention in labelled form, e.g. isotopically labelled, may be used as a diagnostic agent. Examples of such labels are known in the art and include $^{131}$I, $^{35}$S, $^{32}$P, $^{18}$F, $^{14}$C, $^{11}$C, $^{3}$H, and the like.

Another object of the present invention is a process for the preparation of a compound of the Formula (Ia), which process comprises:

a) reacting a compound of Formula (II)

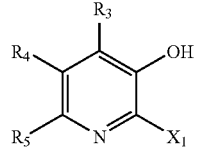

Formula (II)

wherein:
X$_1$ is selected from F, Cl, Br and I,
R$_3$–R$_5$ are each independently H, halogen, methyl or methoxy, provided that at least one of R$_3$-R$_5$ is hydrogen,
with a compound of Formula (III):

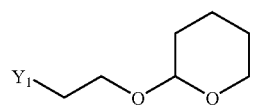

Formula (III)

wherein Y$_1$ is a suitable leaving group selected from Cl, Br, I, OTs, or OMs; in the presence of a base, such as potassium carbonate, triethylamine, or pyridine, in a solvent such as acetonitrile, to give a compound of Formula (IV):

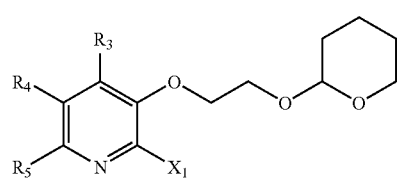

Formula (IV)

wherein X$_1$ and R$_3$–R$_5$ are as defined above;

b) reacting the compound of Formula (IV) with a compound of Formula (Va) in the presence of a base, such as potassium tert-butoxide, in a solvent, such as toluene,

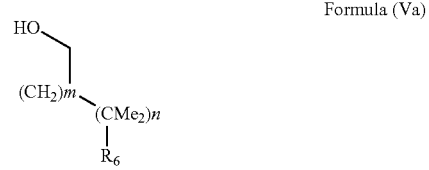

Formula (Va)

wherein:
m is an integer 0–10, preferably 0–7, more preferably 0–5,
n is an integer 0 or 1, wherein the sum of m+n is preferably at least 1,
R$_6$ is NR$_7$R$_8$ or OR$_9$, wherein
R$_7$ and R$_8$ are each independently H or straight or branched C$_1$–C$_4$-alkyl;
or R$_7$ and R$_8$ form together with the nitrogen atom to which they are attached a saturated heterocyclic ring;
R$_9$ is amino-C$_2$–C$_4$-alkyl or N,N-di-C$_1$–C$_4$-alkylamino-C$_2$–C$_4$-alkyl,
to give a compound of Formula (VIa):

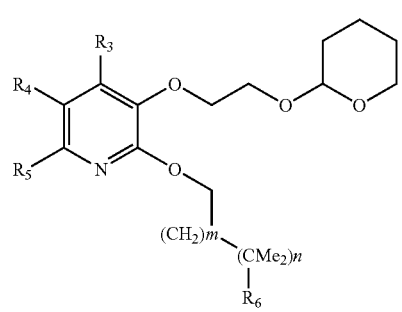

Formula (VIa)

wherein:
R$_3$–R$_6$, m, and n are as defined above, c) treating the compound of Formula (VIa) with an aqueous acid such as aqueous acetic acid or aqueous hydrochloric acid, to give a compound of Formula (VIIa):

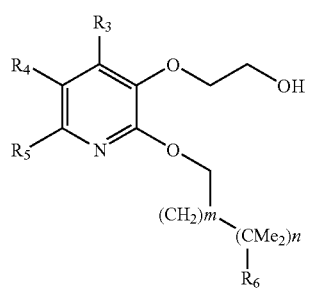

Formula (VIIa)

wherein:
R$_3$–R$_6$, m, and n are as defined above, d) reacting the compound of Formula (VIIa) with a compound of Formula (VIII) in the presence of a base, such as potassium tert-butoxide, in a solvent, such as methyl tert-butyl ether or toluene, Formula (VIII)

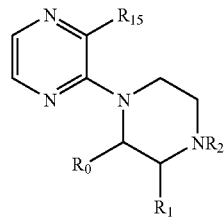

wherein
$R_0$ and $R_1$ are each independently H or $CH_3$;
$R_2$ is selected from $C_1$–$C_4$-alkoxycarbonyl, benzyl, trityl, $C_1$–$C_4$-alkyl, 2-hydroxyethyl, 2-cyanoethyl, tetrahydropyran-2-yl, and $C_1$–$C_4$-acyl,
$R_{15}$ is halogen, such as chlorine, to give a compound of Formula (Ia) wherein X=N and Y=N:

Formula (Ia)

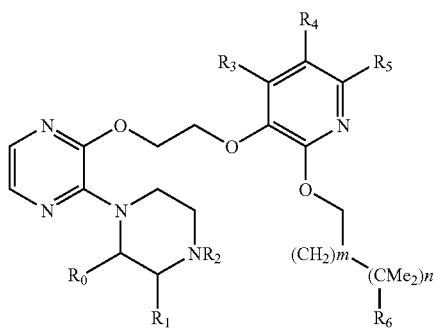

wherein $R_0$–$R_6$, m, and n are as defined above;
e) if desired, separating a racemate obtained into optical isomers and/or forming an acid addition salt with an organic or inorganic acid,
f) if $R_2$ in Formula (Ia) following step d) is a nitrogen protecting group, such as t-BOC, trityl, and benzyl, removing said nitrogen protecting group, such as under acidic conditions (e.g. trifluoroacetic acid in a solvent such as chloroform), hydrogenolytic or non-hydrogenolytic conditions, to provide the compound of Formula (Ia), wherein $R_2$ is hydrogen.

Another object of the present invention is a process for the preparation of a compound of the Formula (Ib), which process comprises:
a) reacting a compound of Formula (II)

Formula (II)

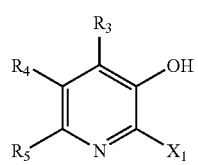

wherein:
$X_1$ is selected from F, Cl, Br and I,
$R_3$–$R_5$ are each independently H, halogen, methyl or methoxy, provided that at least one of $R_3$-$R_5$ is hydrogen, with a compound of Formula (III):

Formula (III)

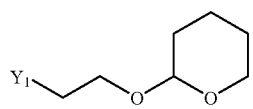

wherein $Y_1$ is a suitable leaving group selected from Cl, Br, I, OTs, or OMs;
in the presence of a base, such as potassium carbonate, triethylamine, or pyridine, in a solvent, such as acetonitrile, to give a compound of Formula (IV):

Formula (IV)

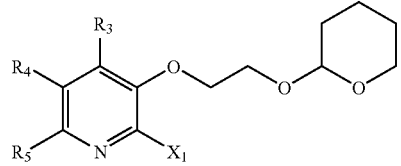

wherein $X_1$ and $R_3$–$R_5$ are as defined above;
b) reacting the compound of Formula (IV) with a compound of Formula (Vb) in the presence of a base, such as potassium tert-butoxide, in a solvent, such as toluene, Formula (Vb)

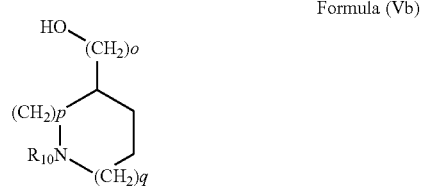

wherein:
o is an integer 0–2;
p is an integer 0–2, wherein o and p are preferably not both 0;
q is an integer 0–1;
$R_{10}$ is H or $C_1$–$C_4$-alkyl, preferably H or methyl;
to give a compound of Formula (VIb):

Formula (VIb)

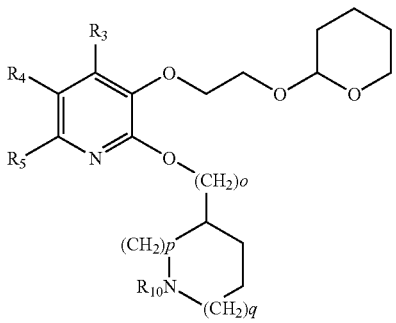

wherein:
$R_3$–$R_5$ and $R_{10}$, o, p, and q are as defined above, c) treating the compound of Formula (VIb) with an aqueous acid such as aqueous acetic acid or aqueous hydrochloric acid, to give a compound of Formula (VIIb):

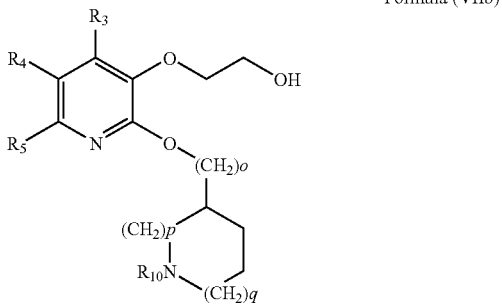

Formula (VIIb)

wherein:
$R_3$–$R_5$ and $R_{10}$, o, p, and q are as defined above, d) reacting the compound of Formula (VIIb) with a compound of Formula (VIII) in the presence of a base such as potassium tert-butoxide, in a solvent, such as methyl tert-butyl ether or toluene,

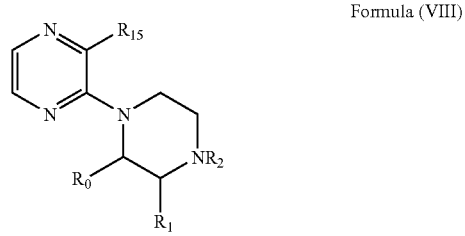

Formula (VIII)

wherein
$R_0$ and $R_1$ are each independently H or $CH_3$;
$R_2$ is selected from $C_1$–$C_4$-alkoxycarbonyl, benzyl, trityl, $C_1$–$C_4$-alkyl, 2-hydroxyethyl, 2-cyanoethyl, tetrahydropyran-2-yl, and $C_1$–$C_4$-acyl,
$R_{15}$ is halogen, such as chlorine, to give a compound of Formula (Ib) wherein X=N and Y=N:

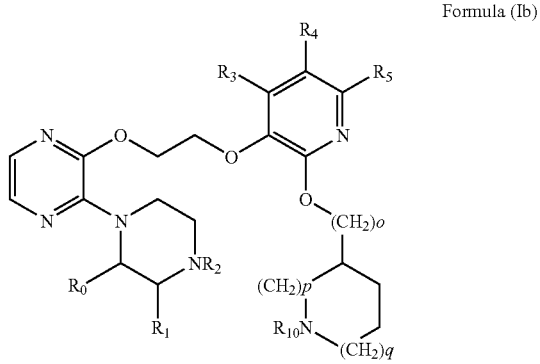

Formula (Ib)

wherein $R_0$–$R_5$, $R_{10}$, o, p, and q are as defined above;

e) if desired, separating a racemate obtained into optical isomers and/or forming an acid addition salt with an organic or inorganic acid, f) if $R_2$ in Formula (Ib) following step d) is a nitrogen protecting group, such as t-BOC, trityl, and benzyl, removing said nitrogen protecting group, such as under acidic conditions (e.g. trifluoroacetic acid in a solvent such as chloroform), hydrogenolytic or non-hydrogenolytic conditions, to provide the compound of Formula (Ib), wherein $R_2$ is hydrogen.

Another object of the present invention is a process for the preparation of a compound of the Formula (Ia), which process comprises:

a) reacting a compound of Formula (IX) with a benzylating agent, such as benzyl chloride, benzyl bromide, or benzyl tosylate, in the presence of a base:

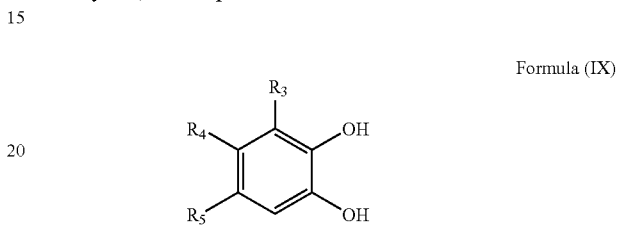

Formula (IX)

wherein $R_3$–$R_5$ are each independently H, halogen, methyl, and methoxy, provided that at least one of $R_3$–$R_5$ is hydrogen, to give a compound of Formula (X):

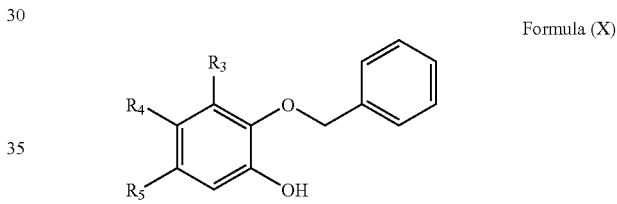

Formula (X)

wherein $R_3$–$R_5$ are as defined above, b) reacting the compound of Formula (X) with a compound of Formula (XIa) in the presence of a base, such as potassium carbonate, in a solvent, such as acetone:

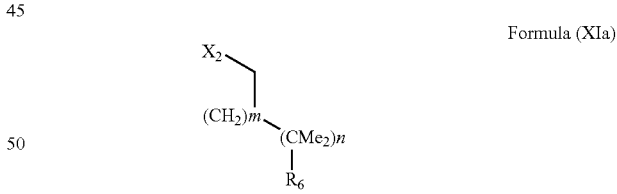

Formula (XIa)

wherein
$X_2$ is halogen, OMs, or OTs;
m is an integer 0–10, preferably 0–7, more preferably 0–5,
n is an integer 0 or 1, wherein the sum of m+n is preferably at least 1,
$R_6$ is $NR_7R_8$ or $OR_9$, wherein
$R_7$ and $R_8$ are each independently H or straight or branched $C_1$–$C_4$-alkyl;
or $R_7$ and $R_8$ form together with the nitrogen atom to which they are attached a saturated heterocyclic ring;
$R_9$ is amino-$C_2$–$C_4$-alkyl or N,N-di-$C_1$–$C_4$-alkylamino-$C_2$–$C_4$-alkyl, to give a compound of Formula (XIIa):

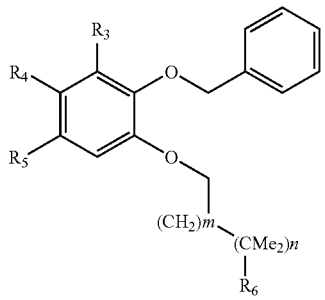

Formula (XIIa)

wherein
R$_3$–R$_6$, m, and n are as defined above;
c) treating the compound of Formula (XIIa) with hydrogen in the presence of a hydrogenation catalyst, such as palladium on carbon, in a solvent, such as methanol, to give a compound of Formula (XIII):

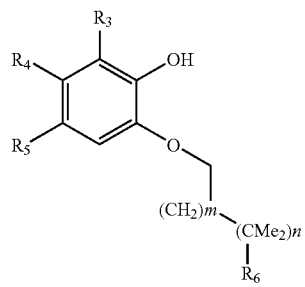

Formula (XIIIa)

wherein R$_3$–R$_6$, m, and n are as defined above;
d) reacting the compound of Formula (XIIIa) with a hydroxyethylating agent such as ethylene carbonate in the presence of a base, such as potassium carbonate, in a solvent, such as N,N-dimethylformamide, to give a compound of Formula (XIVa):

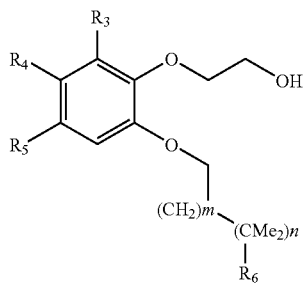

Formula (XIVa)

wherein R$_3$–R$_6$, m, and n are as defined above;
e) reacting the compound of Formula (XIVa) with a compound of Formula (VIII) in the presence of a base such as potassium tert-butoxide, in a solvent, such as N,N-dimethylformamide:

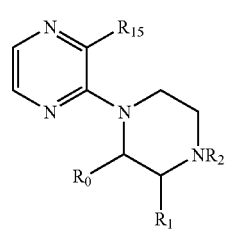

Formula (VIII)

wherein
R$_0$ and R$_1$ are each independently H or CH$_3$;
R$_2$ is selected from C$_1$–C$_4$-alkoxycarbonyl, benzyl, trityl, C$_1$–C$_4$-alkyl, 2-hydroxyethyl, 2-cyanoethyl, tetrahydropyran-2-yl, and C$_1$–C$_4$-acyl,
R$_{15}$ is halogen, such as chlorine, to give a compound of Formula (Ia) wherein X=N and Y=N:

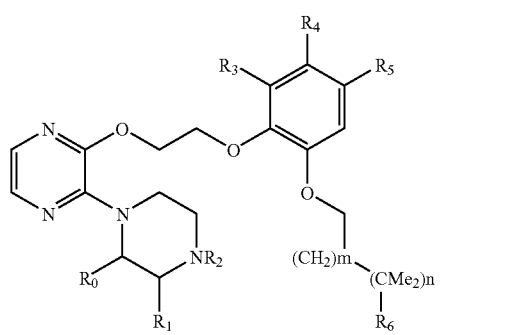

Formula (Ia)

wherein R$_0$–R$_6$, m, and n are as defined above;
f) if desired, separating a racemate obtained into optical isomers and/or forming an acid addition salt with an organic or inorganic acid,
g) if R$_2$ in Formula (Ia) following step e) is a nitrogen protecting group, such as t-BOC, trityl, and benzyl, removing said nitrogen protecting group, such as under acidic conditions (e.g. trifluoroacetic acid in a solvent such as chloroform), hydrogenolytic or non-hydrogenolytic conditions, to provide the compound of Formula (Ia), wherein R$_2$ is hydrogen.

Another object of the present invention is a process for the preparation of a compound of the Formula (Ib), which process comprises:
a) reacting a compound of Formula (IX) with a benzylating agent, such as benzyl chloride, benzyl bromide, or benzyl tosylate, in the presence of a base:

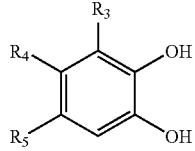

Formula (IX)

wherein R$_3$–R$_5$ are each independently H, halogen, methyl, or methoxy, provided that at least one of R$_3$–R$_5$ is hydrogen, to give a compound of Formula (X):

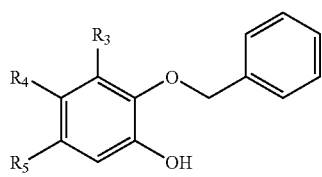

Formula (X)

wherein R$_3$–R$_5$ are as defined above, b) reacting the compound of Formula (X) with a compound of Formula (XIb) in the presence of a base, such as potassium carbonate, in a solvent, such as acetone:

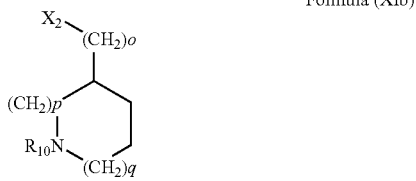
Formula (XIb)

wherein:
$X_2$ is halogen, OMs, or OTs;
o is an integer 0–2;
p is an integer 0–2, wherein o and p are preferably not both 0;
q is an integer 0–1;
$R_{10}$ is H or $C_1$–$C_4$-alkyl, preferably H or methyl;
to give a compound of Formula (XIIb):

Formula (XIIb):

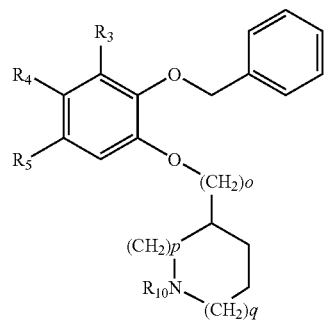

wherein:
$R_3$–$R_5$, $R_{10}$, o, p, and q are as defined above,
c) treating the compound of Formula (XIIb) with hydrogen in the presence of a hydrogenation catalyst, such as palladium on carbon, in a solvent, such as methanol, to give a compound of Formula (XIIIb):

Formula (XIIIb):

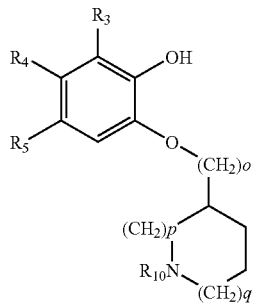

wherein:
$R_3$–$R_5$, $R_{10}$, o, p, and q are as defined above,
d) reacting the compound of Formula (XIIIb) with a hydroxyethylating agent such as ethylene carbonate in the presence of a base, such as potassium carbonate, in a solvent, such as N,N-dimethylformamide, to give a compound of Formula (XIVb):

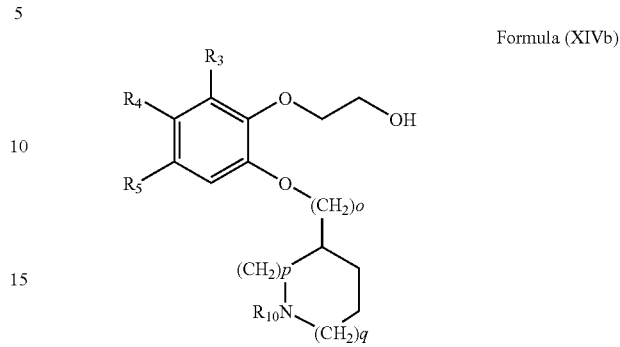
Formula (XIVb)

wherein $R_3$–$R_5$, $R_{10}$, o, p, and q are as defined above;
e) reacting the compound of Formula (XIVa) with a compound of Formula (VIII) in the presence of a base, such as potassium tert-butoxide, in a solvent, such as N,N-dimethylformamide,

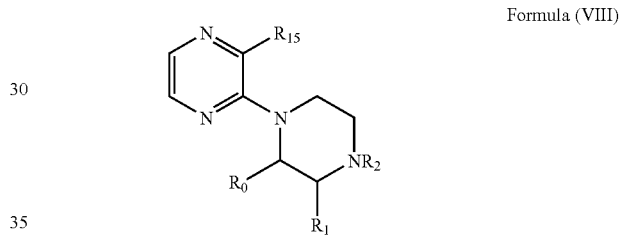
Formula (VIII)

wherein
$R_0$ and $R_1$ are each independently H or $CH_3$;
$R_2$ is selected from $C_1$–$C_4$-alkoxycarbonyl, benzyl, trityl, $C_1$–$C_4$-alkyl, 2-hydroxyethyl, 2-cyanoethyl, tetrahydropyran-2-yl, and $C_1$–$C_4$-acyl,
$R_{15}$ is halogen, such as chlorine, to give a compound of Formula (Ib) wherein X=N and Y=N:

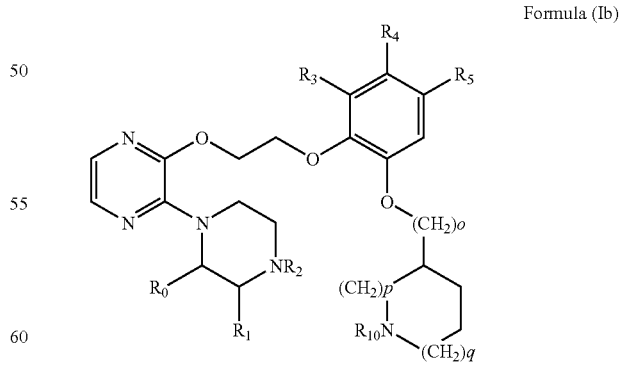
Formula (Ib)

wherein $R_0$–$R_5$, $R_{10}$, o, p, and q are as defined above;
f) if desired, separating a racemate obtained into optical isomers and/or forming an acid addition salt with an organic or inorganic acid, g) if $R_2$ in Formula (Ib) following step e) is a nitrogen protecting group, such as t-BOC, trityl, and benzyl, removing said nitrogen protecting group, such as under acidic conditions (e.g., trifluoroacetic acid in a solvent such as chloroform), hydrogenolytic or non-hydrogenolytic conditions, to provide the compound of Formula (Ib), wherein $R_2$ is hydrogen.

Another object of the present invention is a process for the preparation of a compound of the Formula (Ia), which process comprises:

a) reacting a compound of Formula (XV) with a compound selected from benzyl chloride, benzyl bromide, benzyl iodide, benzyl tosylate, and benzyl mesylate in the presence of a base, such as potassium carbonate, in a solvent, such as N,N-dimethylformamide,

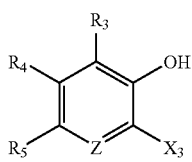

Formula (XV)

wherein:
$X_3$ is selected from Cl, Br and I, Z is CH or N,
$R_3$–$R_5$ are each independently H, halogen, methyl or methoxy, provided that at least one of $R_3$-$R_5$ is hydrogen, to give a compound of Formula (XVI):

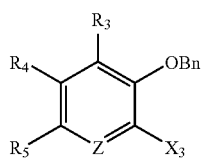

Formula (XVI)

wherein $R_3$–$R_5$, $X_3$, and Z are as defined above;

b) reacting the compound of Formula (XVI) with a compound of Formula (Va) in the presence of a base, such as sodium tert-butoxide, in a solvent, such as N,N-dimethylformamide,

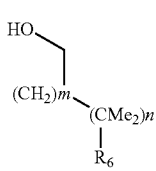

Formula (Va)

wherein:
m is an integer 0–10, preferably 0–7, more preferably 0–5,
n is an integer 0 or 1, wherein the sum of m+n is preferably at least 1,
$R_6$ is $NR_7R_8$ or $OR_9$, wherein
$R_7$ and $R_8$ are each independently H or straight or branched $C_1$–$C_4$-alkyl;
or $R_7$ and $R_8$ form together with the nitrogen atom to which they are attached a saturated heterocyclic ring;

$R_9$ is amino-$C_2$–$C_4$-alkyl or N,N-di-$C_1$–$C_4$-alkylamino-$C_2$–$C_4$-alkyl, to give a compound of Formula (XVIIa):

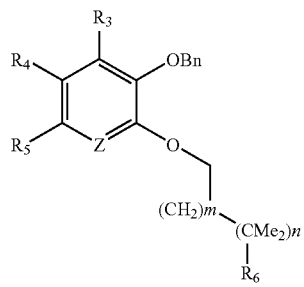

Formula (XVIIa)

wherein:
$R_3$–$R_6$, m, n, and Z are as defined above, c) treating the compound of Formula (XVIIa) with a hydrogenation catalyst using a suitable hydrogen source such as ammonium formate and then heating in the presence of a hydroxyethylating agent, preferably ethylene carbonate, and a base, such as potassium carbonate, in a solvent, such as N,N-dimethylformamide, to give a compound of Formula (VIIa):

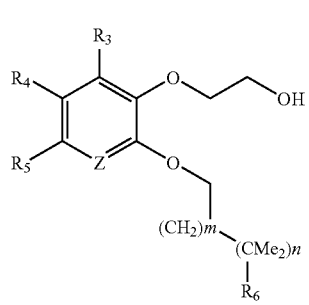

Formula (VIIa)

wherein:
$R_3$–$R_6$, m, n, and Z are as defined above, d) reacting the compound of Formula (VIIa) with a compound of Formula (VIII) in the presence of a base, such as sodium tert-butoxide, in a solvent, such as N,N-dimethylformamide,

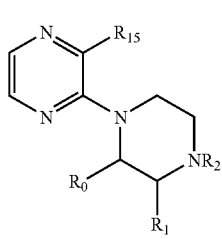

Formula (VIII)

wherein
$R_0$ and $R_1$ are each independently H or $CH_3$;
$R_2$ is selected from $C_1$–$C_4$-alkoxycarbonyl, benzyl, trityl, $C_1$–$C_4$-alkyl, 2-hydroxyethyl, 2-cyanoethyl, tetrahydropyran-2-yl, and $C_1$–$C_4$-acyl, $R_{15}$ is halogen, such as chlorine, to give a compound of Formula (Ia) wherein X=N and Y=N:

Formula (Ia)

wherein $R_0$–$R_6$, m, n, and Z are as defined above;

e) if desired, separating a racemate obtained into optical isomers and/or forming an acid addition salt with an organic or inorganic acid, f) if $R_2$ in Formula (Ia) following step d) is a nitrogen protecting group, such as t-BOC, trityl, and benzyl, removing said nitrogen protecting group, such as under acidic conditions (e.g. trifluoroacetic acid in a solvent such as chloroform), hydrogenolytic or non-hydrogenolytic conditions, to provide the compound of Formula (Ia), wherein $R_2$ is hydrogen.

Another object of the present invention is a process for the preparation of a compound of the Formula (Ib), which process comprises:

a) reacting a compound of Formula (XV) with a compound selected from benzyl chloride, benzyl bromide, benzyl iodide, benzyl tosylate, and benzyl mesylate in the presence of a base, such as potassium carbonate, in a solvent, such as N,N-dimethylformamide, Formula (XV)

wherein:
$X_1$ is selected from Cl, Br and I, Z is CH or N,
$R_3$–$R_5$ are each independently H, halogen, methyl or methoxy, provided that at least one of $R_3$-$R_5$ is hydrogen, to give a compound of Formula (XVI):

Formula (XVI)

wherein $R_3$–$R_5$, $X_3$, and Z are as defined above;

b) reacting the compound of Formula (XVI) with a compound of Formula (Vb) in the presence of a base, such as sodium tert-butoxide, in a solvent, such as N,N-dimethylformamide, Formula (Vb)

wherein:
o is an integer 0–2;
p is an integer 0–2, wherein o and p are preferably not both 0;
q is an integer 0–1;
$R_{10}$ is H or $C_1$–$C_4$-alkyl, preferably H or methyl;
to give a compound of Formula (XVIIb):

Formula (XVIIb)

wherein:
$R_3$–$R_5$ and $R_{10}$, o, p, q, and Z are as defined above, c) treating the compound of Formula (XVIIb) with a hydrogenation catalyst using a suitable hydrogen source such as ammonium formate and then heating in the presence of a hydroxyethylating agent, preferably ethylene carbonate, and a base, such as potassium carbonate, in a solvent, such as N,N-dimethylformamide, to give a compound of Formula (VIIb):

Formula (VIIb)

wherein:
$R_3$–$R_5$ and $R_{10}$, o, p, q, and Z are as defined above, d) reacting the compound of Formula (VIIb) with a compound of Formula (VIII) in the presence of a base such as sodium tert-butoxide, in a solvent, such as N,N-dimethylformamide,

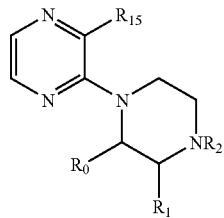

Formula (VIII)

wherein
R$_0$ and R$_1$ are each independently H or CH$_3$;
R$_2$ is selected from C$_1$–C$_4$-alkoxycarbonyl, benzyl, trityl, C$_1$–C$_4$-alkyl, 2-hydroxyethyl, 2-cyanoethyl, tetrahydropyran-2-yl, and C$_1$–C$_4$-acyl,
R$_{15}$ is halogen, such as chlorine, to give a compound of Formula (Ib) wherein X=N and Y=N:

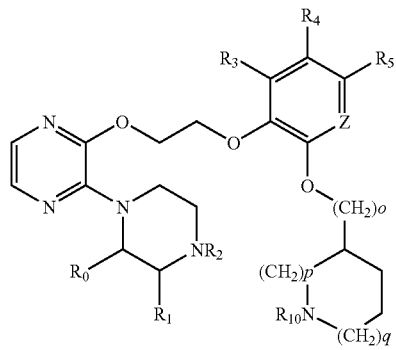

Formula (Ib)

wherein R$_0$–R$_5$, R$_{10}$, o, p, q, and Z are as defined above;
e) if desired, separating a racemate obtained into optical isomers and/or forming an acid addition salt with an organic or inorganic acid,
f) if R$_2$ in Formula (Ib) following step d) is a nitrogen protecting group, such as t-BOC, trityl, and benzyl, removing said nitrogen protecting group, such as under acidic conditions (e.g. trifluoroacetic acid in a solvent such as chloroform), hydrogenolytic or non-hydrogenolytic conditions, to provide the compound of Formula (Ib), wherein R$_2$ is hydrogen.

Another object of the present invention is a process for the preparation of a compound of the Formula (Ic), which process comprises:
a) reacting a compound of formula (XVIII):

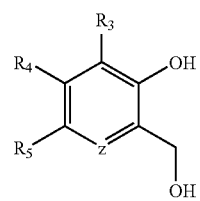

Formula (XVIII)

wherein:
R$_3$–R$_5$ are each independently H, halogen, methyl or methoxy, provided that at least one of R$_3$-R$_5$ is hydrogen;
Z is CH or N, with a compound of Formula (III):

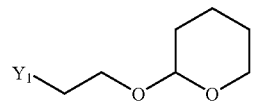

Formula (III)

wherein Y$_1$ is a suitable leaving group selected from Cl, Br, I, OTs, or OMs;
in the presence of a base, such as potassium carbonate, triethylamine, or pyridine, in a solvent, such as acetonitrile, to give a compound of Formula (XIX):

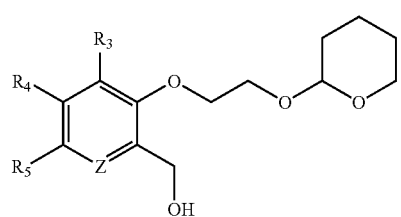

Formula (XIX)

wherein R$_3$–R$_5$ and Z are as defined above,
b) transforming the alcohol function in the compound of Formula (XVI) into an aldehyde function with dimethyl sulfoxide and oxalyl chloride in dichloromethane, to give a compound of Formula (XX):

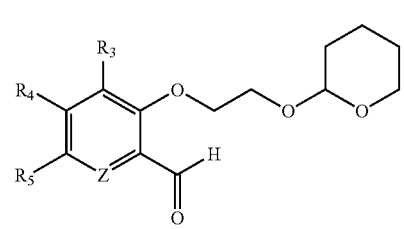

Formula (XX)

wherein:
R$_3$–R$_5$ and Z are as defined above,
c) reacting the compound of Formula (XX) with a compound of Formula (XXI) in the presence of a base, such as potassium tert-butoxide in a solvent mixture consisting of tetrahydrofuran and tert-butanol,

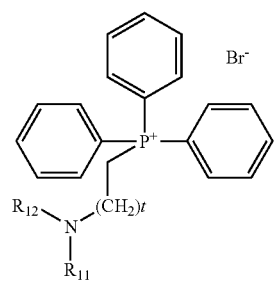

Formula (XXI)

wherein:
t is an integer 1–11, preferably 1–8, more preferably 1–6, most preferably 1; and $R_{11}$ and $R_{12}$ are each independently H or straight or branched $C_1$–$C_4$-alkyl; or $R_{11}$ and $R_{12}$ form together with the nitrogen atom to which they are attached a saturated heterocyclic ring, to give a compound of Formula (XXII):

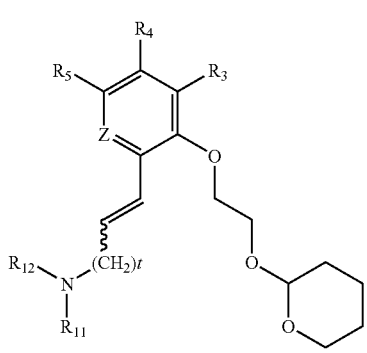

Formula (XXII)

wherein:
$R_3$–$R_5$, $R_{11}$, $R_{12}$, t, and Z are as defined above;
the orientation around the double bond may be either cis or trans;

d) separation by preparative HPLC and isolation of the cis and trans isomers of compound of Formula (XXII) to provide the individual cis isomer of Formula (XXIII) and the individual trans isomer of Formula (XXIV)

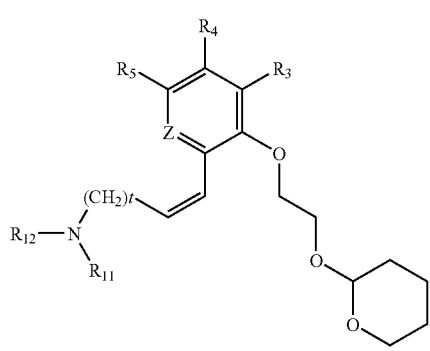

Formula (XXIII)

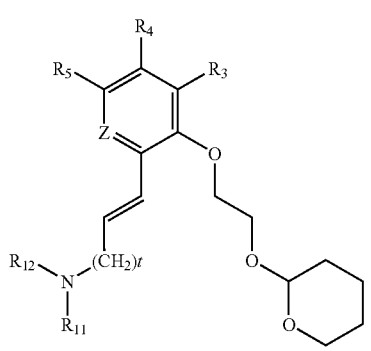

Formula (XXIV)

wherein:
$R_3$–$R_5$, $R_{11}$, $R_{12}$, t, and Z are as defined above;

e) treating the compounds of Formula (XXIII) and (XXIV), respectively, with an aqueous acid such as aqueous acetic acid or aqueous hydrochloric acid, to give compounds of Formula (XXV) and (XXVI), respectively:

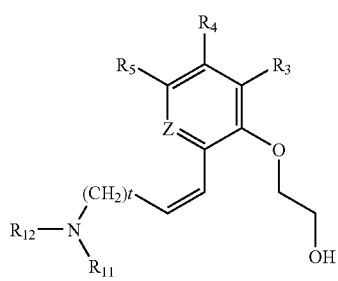

Formula (XXV)

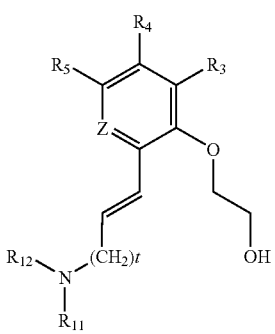

Formula (XXVI)

wherein:
$R_3$–$R_5$, $R_{11}$, $R_{12}$, t, and Z are as defined above;

f) reacting the compounds of Formula (XXV) and (XXVI) with a compound of Formula (VIII) in the presence of a base, such as potassium tert-butoxide, in a solvent, such as N,N-dimethylformamide:

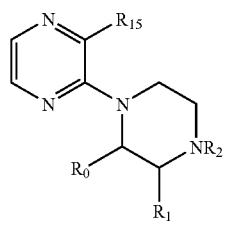

Formula (VIII)

wherein
$R_0$ and $R_1$ are each independently H or $CH_3$;
$R_2$ is selected from $C_1$–$C_4$-alkoxycarbonyl, benzyl, trityl, $C_1$–$C_4$-alkyl, 2-hydroxyethyl, 2-cyanoethyl, tetrahydropyran-2-yl, and $C_1$–$C_4$-acyl, $R_{15}$ is halogen, such as chlorine, to give compounds of Formula (XXVII) and (XXVIII):

Formula (XXVII)

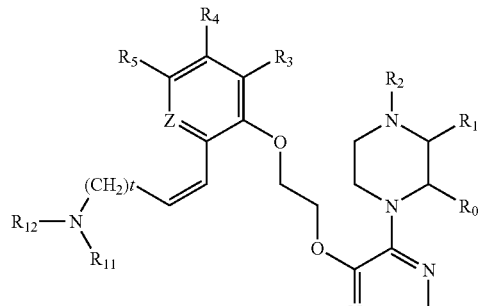

Formula (XXVIII)

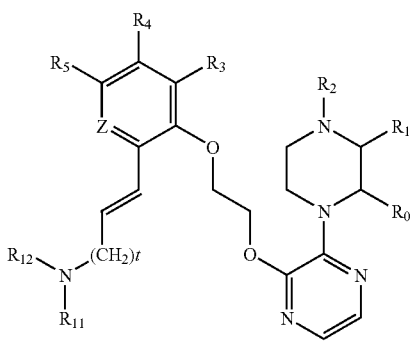

wherein:
$R_0$–$R_5$, $R_{11}$, $R_{12}$, t, and Z are as defined above;
wherein the compounds of Formula (XXVII) and (XXVIII) are isomers of the compound of Formula (Ic) wherein X=N and Y=N;

g) if $R_2$ in Formula (Ic) following step f) is a nitrogen protecting group, such as t-BOC, trityl, and benzyl, removing said nitrogen protecting group, such as under acidic conditions (e.g. trifluoroacetic acid in a solvent such as chloroform), hydrogenolytic or non-hydrogenolytic conditions, to provide the compound of Formula (Ic), wherein $R_2$ is hydrogen.

Another object of the present invention is a process for the preparation of a compound of the Formula (Id), which process comprises:

a) treating the compound of Formula (XXII) with hydrogen in the presence of a hydrogenation catalyst, such palladium on carbon, in a solvent, such as methanol, to give a compound of Formula (XXIX):

Formula (XXIX)

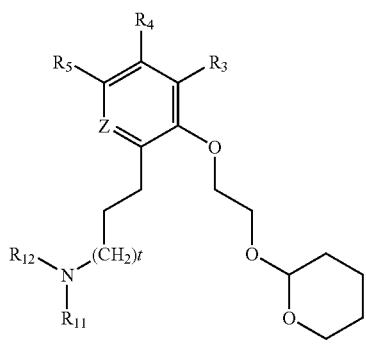

wherein:
$R_3$–$R_5$ are each independently H, halogen, methyl, and methoxy, provided that at least one of $R_3$–$R_5$ is hydrogen, Z is CH or N,
t is an integer 1–11, preferably 1–8, more preferably 1–6, most preferably 1; and
$R_{11}$ and $R_{12}$ are each independently H or straight or branched $C_1$–$C_4$-alkyl; or $R_{11}$ and $R_{12}$ form together with the nitrogen atom to which they are attached a saturated heterocyclic ring;

b) treating the compound of Formula (XXIX) with an aqueous acid such as aqueous acetic acid or aqueous hydrochloric acid, to give a compound of Formula (XXX):

Formula (XXX)

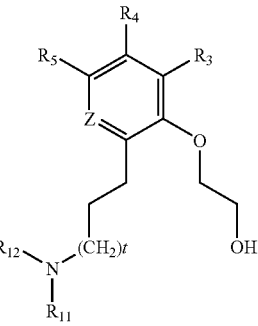

wherein:
$R_3$–$R_5$, $R_{11}$, $R_{12}$, t, and Z are as defined above;

c) reacting the compound of Formula (XXX) with a compound of Formula (VIII) in the presence of a base, such as potassium tert-butoxide, in a solvent, such as N,N-dimethylformamide or dioxane:

Formula (VIII)

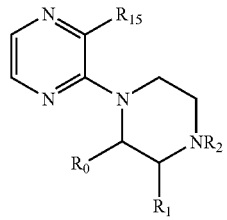

wherein
$R_0$ and $R_1$ are each independently H or $CH_3$;
$R_2$ is selected from $C_1$–$C_4$-alkoxycarbonyl, benzyl, trityl, $C_1$–$C_4$-alkyl, 2-hydroxyethyl, 2-cyanoethyl, tetrahydropyran-2-yl, and $C_1$–$C_4$-acyl,
$R_{15}$ is halogen, such as chlorine, to give a compound of Formula (XXXI):

Formula (XXXI):

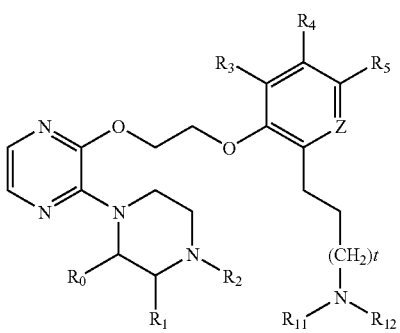

wherein:

$R_0$–$R_5$, $R_{15}$, $R_{12}$, t, and Z are as defined above; wherein Formula (XXXI) corresponds to Formula (Id) wherein W=CH$_2$, r=t, X=N, Y=N, $R_{13}$=$R_{11}$, and $R_{14}$=$R_{12}$, d) if $R_2$ in Formula (Id) following step c) is a nitrogen protecting group, such as t-BOC, trityl, and benzyl, removing said nitrogen protecting group, such as under acidic conditions (e.g. trifluoroacetic acid in a solvent such as chloroform), hydrogenolytic or non-hydrogenolytic conditions, to provide the compound of Formula (Id), wherein $R_2$ is hydrogen.

Another object of the present invention is a process for the preparation of a compound of the Formula (Id), which process comprises:

a) reacting a compound of Formula (XVIII):

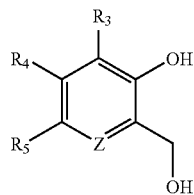

Formula (XVIII)

wherein:

$R_3$–$R_5$ are each independently H, halogen, methyl or methoxy, provided that at least one of $R_3$-$R_5$ is hydrogen;

Z is CH or N, with a compound of Formula (III):

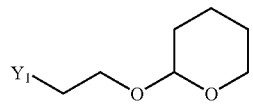

Formula (III)

wherein $Y_1$ is a suitable leaving group selected from Cl, Br, I, OTs, or OMs; in the presence of a base, such as potassium carbonate, triethylamine, or pyridine, in a solvent, such as acetonitrile, to give a compound of Formula (XIX):

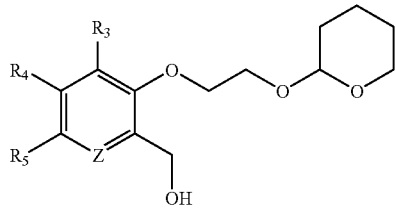

Formula (XIX)

wherein $R_3$–$R_5$ and Z are as defined above, b) transforming the alcohol function in Formula (XIX) into a suitable leaving group, e.g. by treatment with methanesulfonic anhydride in the presence of triethylamine in dichloromethane, to give a compound of Formula (XXXII):

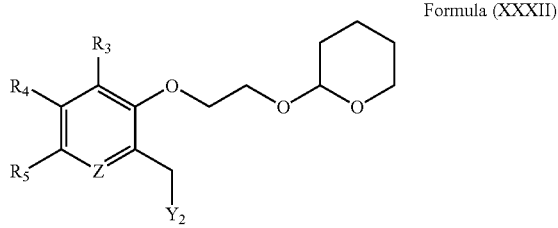

Formula (XXXII)

wherein $R_3$–$R_5$, and Z are as defined above;

$Y_2$ is halogen, OMs, or OTs;

c) reacting the compound of Formula (XXXII) with a compound of Formula (XXXIII) in the presence of a base, such as potassium tert-butoxide, in a solvent, such as dioxane:

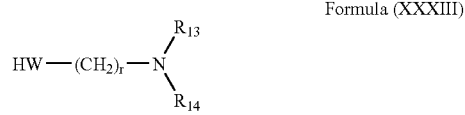

Formula (XXXIII)

wherein:

W is O;

r is an integer of 1–11, preferably 1–8, more preferably 1–6, most preferably 2;

$R_{13}$ and $R_{14}$ are each independently H or straight or branched $C_1$–$C_4$-alkyl; or $R_{13}$ and $R_{14}$ form together with the nitrogen atom to which they are attached a saturated heterocyclic ring, to give a compound of Formula (XXXIV):

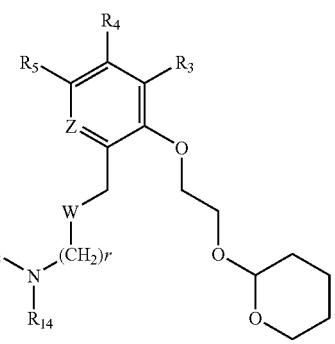

Formula (XXXIV)

wherein:

r, z, W, $R_3$–$R_5$, and $R_{13}$ and $R_{14}$ are as described above;

d) treating the compound of Formula (XXXIV) with an aqueous acid such as aqueous acetic acid or aqueous hydrochloric acid, to give a compound of Formula (XXXV):

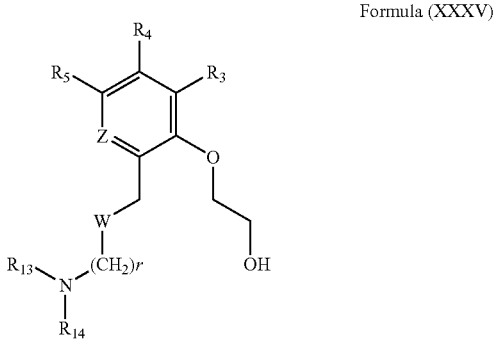

Formula (XXXV)

wherein:
r, z, W, $R_3$–$R_5$, and $R_{13}$ and $R_{14}$ are as described above;

e) reacting the compound of Formula (XXXV) with a compound of Formula (VIII) in the presence of a base, such as potassium tert-butoxide, in a solvent, such as N,N-dimethylformamide:

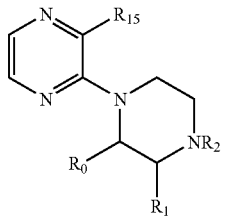

Formula (VIII)

wherein
$R_0$ and $R_1$ are each independently H or $CH_3$;
$R_2$ is selected from $C_1$–$C_4$-alkoxycarbonyl, benzyl, trityl, $C_1$–$C_4$-alkyl, 2-hydroxyethyl, 2-cyanoethyl, tetrahydropyran-2-yl, and $C_1$–$C_4$-acyl,
$R_{15}$ is halogen, such as chlorine, to give a compound of Formula (XXXVI):

Formula (XXXVI):

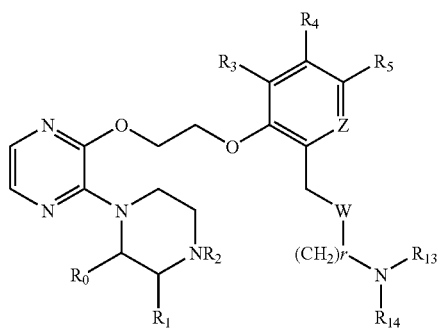

wherein:
$R_0$–$R_5$, $R_{13}$, $R_{14}$, r, W, and Z are as defined above; wherein Formula (XXXVI) corresponds to Formula (Id) wherein X=N and Y=N, f) if $R_2$ in Formula (Id) following step e) is a nitrogen protecting group, such as t-BOC, trityl, and benzyl, removing said nitrogen protecting group, such as under acidic conditions (e.g. trifluoroacetic acid in a solvent such as chloroform), hydrogenolytic or non-hydrogenolytic conditions, to provide the compound of Formula (Id), wherein $R_2$ is hydrogen.

The chemicals used in the above-described synthetic routes may include, for example, solvents, reagents, catalysts, protecting group and deprotecting group agents. The methods described above may also additionally include steps, either before or after the steps described specifically herein, to add or remove suitable protecting groups in order to ultimately allow synthesis of the compounds of Formulae (I). In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Examples of protecting groups according to the present invention are t-BOC (tert-butoxycarbonyl), trityl, and benzyl.

It should be noted that a compound of Formula (I) (including any of Formulae Ia, Ib, Ic and Id) as prepared according to the present invention may be converted to another compound of Formula (I) by methods well known in the art. For example, a standard reductive alkylation reaction is illustrated in Example 17 by the preparation of a compound of Formula (I) wherein $R_2$ is methyl from the corresponding compound of Formula (I) wherein $R_2$ is hydrogen (cf. the protocol described in J. Org. Chem. 1996, 61, 3849–3862).

The processes described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are maleic acid, fumaric acid, succinic acid, methanesulfonic acid, trifluoroacetic acid, acetic acid, oxalic acid, benzoic acid, malic acid, hydrochloric acid, sulphuric acid, phosphoric acid, isethionic acid, and the like.

The compounds of Formulae (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The necessary starting materials for preparing the compounds of Formulae (I) are either known or may be prepared in analogy with the preparation of known compounds.

In accordance with the present invention, the compounds of Formulae (I), in the form of free bases or salts with physiologically acceptable acids, can be brought into suitable galenic forms, such as compositions for oral use, for injection, for nasal spray administration or the like, in accordance with accepted pharmaceutical procedures. Such pharmaceutical compositions according to the invention comprise an effective amount of the compounds of Formulae (I) in association with compatible pharmaceutically acceptable carrier materials, or diluents, as are well known in the art. The carriers may be any inert material, organic or inorganic, suitable for enteral, percutaneous, subcutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavouring agents, buffers, and the like.

The compositions according to the invention can e.g. be made up in solid or liquid form for oral administration, such as tablets, pills, capsules, powders, syrups, elixirs, dispersable granules, cachets, suppositories and the like, in the form of sterile solutions, suspensions or emulsions for parenteral administration, sprays, e.g. a nasal spray, transdermal preparations, e.g. patches, and the like.

As mentioned above, the compounds of the invention may be used for the treatment of a human or animal subject suffering from a scrotonin-related disorder or condition, particularly 5-HT$_{2C}$ receptor-related, such as memory disorders, such as Alzheimer's disease; schizophrenia; mood disorders such as depression; anxiety disorders; pain; substance abuse; sexual dysfunctions such as erectile dysfunction; epilepsy; glaucoma; urinary disorders, such as urinary incontinence; menopausal and post-menopausal hot flushes; type 2 diabetes; eating disorders, such as binge eating disorders, anorexia nervosa and bulimia; weight gain associated with antipsychotic drug administration, premenstrual tension, sleep disorders; and particularly obesity.

This invention also relates to a method of treatment or prophylaxis of a serotonin-related disorder or condition as described above. The method includes administering to a subject (e.g., a human, a horse, a dog, or a cat) in need thereof an effective amount of one or more compounds of Formulae (I) described above. The methods delineated herein can also include the step of identifying that the subject is in need of treatment of the serotonin-related disorder or condition.

Also within the scope of this invention is a method for modulating (e.g., stimulating or inhibiting) 5-HT$_{2C}$ receptor function. The method includes contacting the receptor with an effective stimulatory or inhibitory amount of a compound of Formula (I), preferably an effective stimulatory amount thereof. The contacting step can include administering a compound, its salt, or a composition containing the compound or the salt.

"An effective amount" refers to an amount of a compound which confers a therapeutic effect on the treated subject. The therapeutic effect may be objective (i.e., measurable by some test or marker) or subjective (i.e., subject gives an indication of or feels an effect). The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

The invention will now be further illustrated by the following non-limiting Examples. Without further elaboration, it is believed that one skilled in the art can, based on the description herein, utilize the present invention to its fullest extent. All publications cited herein are hereby incorporated by reference in their entirety.

EXAMPLES

General

Unless otherwise noted, starting materials were obtained from commercial sources and used as received. $^1$H nuclear magnetic resonance (NMR) and $^{13}$C NMR spectra were recorded on a Bruker Advance DPX 400 spectrometer at 400.1 and 100.6 MHz, respectively, or on a JEOL 270 spectrometer. All spectra were recorded using residual solvent as internal standard. Melting points were determined with a Koefler bench and are uncorrected. Electrospray mass spectrometry (MS) spectra were obtained on a Perkin-Elmer API 150EX mass spectrometer. Accurate mass measurements were performed on a Micromass LCT dual probe.

HPLC (High-Performance Liquid Chromatography) Conditions for Example 1 and Example 2:

The preparative LC was performed on a preparative LC-MS Gilson-Finnigan with a 50×20 mm S 5 μm, 120A column. The flow was 30 mL/min and different gradients of 0.1% acetic acid in water and acetonitrile were used.

HPLC Conditions for Examples 3–16:

Preparative HPLC was Performed on a Gilson-system equipped with an YMC AQ C18, 5 μm column (20×50 mm), eluent: water/acetonitrile+0.1% trifluoroacetic acid. Analytical LC-UV was performed on an Agilent 1100 system with an ACE C8, 3 μm column (3×50 mm), eluent: water/acetonitrile+0.1% trifluoroacetic acid. Analytical LC-MS was performed on an Agilent 1100 system with an YMC AQ C18, 3 μm column (3×33 mm), eluent: water/acetonitrile+0.1% trifluoroacetic acid.

HPLC Conditions for Examples 17–27:

Preparative HPLC/MS was performed on a Waters/Micromass Platform ZQ system equipped with System A: ACE 5 C8 column (19×50 mm), eluent: 0.1% TFA in different gradients of MilliQ water and MeCN. System B: Xterra MS C18, μm column (19×50 mm), eluent: 10 mM NH$_4$HCO$_3$/ NH$_3$ buffer pH 10 in different gradients of MilliQ water and MeCN. Analytical HPLC were performed on Agilent 1100, column: ACE 3 C8 (system A) or column: YMC-Pack (system B), eluents: MilliQ/0.1%TFA and MeCN. Preparative flash chromatography was performed on Merck silica gel 60 (230–400 mesh). GC-MS analysis were performed on a Hewlett Packard 5890 gas chromatograph with a HP-5MS 15 m×0.25 mm×0.25 μm column connected to a 5971 MS detector.

Example 1

N,N-Dimethyl-(2-(3-[2-(2-(R)-methyl-3,4,5,6-tetrahydro-2H-[1,2']bipyrazinyl-3'-yloxy)-ethoxy]-pyridin-2-yloxy)-ethyl)-amine, acetate Step 1: 3-Benzyloxy-2-bromopyridine*

A mixture of 2-bromo-pyridine-3-ol (50.4 g, 0.29 mol), benzyl bromide (45.5 g, 0.28 mol) and potassium carbonate (52 g, 0.38 mol) in dry N,N-dimethylformamide (DMF; 300 mL) was heated at 110° C. for 30 minutes. The mixture was filtered through a pad of Celite®, the solvent was removed under reduced pressure and the black residue was taken up between ice cold 0.5 M aqueous NaOH and EtOAc. The organic phase was washed twice with brine, dried (MgSO$_4$), and concentrated under reduced pressure to yield 69.6 g (93%) of the title compound as a brown oil. HRMS m/z calcd for $C_{12}H_{10}BrNO$ (M)$^+$ 263.9946. found 263.9939. *Previously described in J. Med. Chem. 1996, 39, 5267–5275.

Step 2: 2-{[3-(Benzyloxy)pyridin-2-yl]oxy}-N,N-dimethylethanamine.

To a mixture of N,N-dimethylaminoethanol (4.16 g, 46.7 mmol) and (3-benzyloxy)-2-bromopyridine (from Step 1; 8.22 g, 31.1 mmol) in dry DMF (50 mL) was sodium tert-butoxide (5.98 g, 62.2 mmol) added in one portion. The reaction mixture was stirred at 80° C. for 1.5 h, the solvent was removed under reduced pressure and the oily residue was taken up between CHCl$_3$/water. The aqueous phase was extracted twice with CHCl$_3$ and the combined organic layers were washed once with brine, dried (MgSO$_4$), and concentrated under reduced pressure. This gave 8.4 g (100%) of the title compound as a light brown oil. Purity 95% (HPLC). HRMS m/z calcd for $C_{16}H_{20}N_2O_2$ (M)$^+$ 272.1525. found 272.1537.

Step 3: 2-[2-(2-Dimethylamino-ethoxy)-pyridine-3-yloxy-]-ethanol.

To a N$_2$-flushed solution of 2-{[3-(benzyloxy)pyridin-2-yl]oxy}-N,N-dimethylethanamine (from Step 2; 8.4 g, 31.1 mmol) in MeOH (100 mL) was added 10% Pd/C (0.8 g) followed by ammonium fornate (6.3 g, 100 mmol). The mixture was stirred at 50° C. under an atmosphere of nitrogen for 2 h. The reaction was filtered through Celite® and the solvent was removed under reduced pressure to yield a semi-crystalline material that was used without further purification in the next synthetic step. The crude product was dissolved in dry DMF (50 mL), potassium carbonate (6.0 g, 43 mmol) was added and the mixture was heated at 150° C. for 20 minutes. Ethylene carbonate (4.1 g, 46 mmol) was added and the heating was continued for another 1.5 h. Solids were filtered off and the filtrate was concentrated under reduced pressure. The residue was chromatographed on a column of silica using CHCl$_3$/MeOH/NH$_4$OH (95:5: 0.2) as eluent to give 3.28 g (31%) of the title product as a light brown oil. HRMS m/z calcd for $C_{11}H_{18}N_2O_3$ (M)$^+$ 226.1317. found 226.1323.

Step 4: N,N-Dimethyl-(2-(3-[2-(2-(R)-methyl-3,4,5,6-tetrahydro-2H-[1,2']bipyrazinyl-3'-yloxy)-ethoxy]-pyridin-2-yloxy)-ethyl)-amine, acetate.

To a solution of 2-[2-(2-dimethylamino-ethoxy)-pyridine-3-yloxy]-ethanol (from Step 3; 2.89 g, 12.8 mmol) in DMF (50 mL) was sodium tert-butoxide (1.84 g, 19.2 mmol) added in one portion and the reaction was stirred at room temperature for 10 minutes. To the mixture was (2R)-1-(3-chloro-2-pyrazinyl)-2-methylpiperazine* (2.81 g, 13.5 mmol) added and the reaction was stirred at 60° C. for 30 minutes. Silica (~15 g) was added and the mixture was filtered through a short plug of silica. The solvent was evaporated under reduced pressure and the residue was chromatographed on a column of silica using CHCl$_3$/MeOH/ NH$_4$OH (95:5:0.2 followed by 90:10:0.2) as eluent. The solvent from the pure combined fractions was evaporated off under reduced pressure and the residue was dissolved in ether and HOAc in ether was added. After 15 h in the refrigerator white crystals could be filtered off and dried (60° C., 1 mm Hg) to give 2.5 g (42%) of the title compound: mp 75° C. Fragmenting MS analysis supports the stated structure. HRMS m/z calcd for $C_{20}H_{30}N_6O_3$ (M)$^+$ 402.2379. found 402.2383. *Prepared as described in WO 00/76984, Example 192, Step 2.

Example 2

N,N-Diisopropyl-(2-(3-[2-(2-(R)-methyl-3,4,5,6-tetrahydro-2H-[1,2']bipyrazinyl-3'-yloxy)-ethoxy]-pyridin-2-yloxy)-ethyl)-amine, acetate Step 1: (2-{[3-(Benzyloxy)pyridin-2-yl]oxy}ethyl)diisopropylamine.

To a mixture of N,N-diisopropylaminoethanol (4.07 g, 28.0 mmol) and (3-benzyloxy)-2-bromopyridine (from Example 1, Step 1; 6.16 g, 23.3 mmol) in dry DMF (50 mL) was sodium tert-butoxide (3.36 g, 35.0 mmol) added in one portion. The reaction mixture was stirred at 80° C. for 1.5 h. Silica (~15 g) was added and the mixture was filtered. The solvent was evaporated off under reduced pressure and the remaining oil was chromatographed on a column of silica using toluene/Et$_3$N (97:3) as eluent to give 5.8 g (76%) of the title compound as a light brown oil. Purity 85% (HPLC). Fragmenting MS analysis supports the stated structure. HRMS m/z calcd for $C_{20}H_{28}N_2O_2$ (M)$^+$ 328.2151. found 328.2142.

Step 2: 2-[2-(2-Diisopropylamino-ethoxy)-pyridine-3-yloxy-]-ethanol.

The title compound was prepared starting from (2-{[3-(benzyloxy)pyridin-2-yl]oxy}ethyl)diisopropylamine (from Step 1; 5.0 g, 15.2 mmol) using the procedure given in Example 1, Step 3. This produced 1.8 g (42%) of the title compound as a light brown oil. Purity 91% (HPLC). Fragmenting MS analysis supports the stated structure. HRMS m/z calcd for $C_{15}H_{26}N_2O_3$ (M)$^+$ 282.1943. found 282.1948.

Step 3: N,N-Diisopropyl-(2-(3-[2-(2-(R)-methyl-3,4,5,6-tetrahydro-2H-[1,2']bipyrazinyl-3'-yloxy)-ethoxy]-pyridin-2-yloxy)-ethyl)-amine, acetate.

The title compound was prepared starting from 2-[2-(2-diisopropylamino-ethoxy)-pyridine-3-yloxy]-ethanol (1.52 g, 5.30 mmol) and (2R)-1-(3-chloro-2-pyrazinyl)-2-methylpiperazine* (1.24 g, 5.83 mmol) using the procedure given Example 1, Step 4. The crude product was chromatographed on a column of silica using CHCl$_3$/MeOH/aqueous concentrated NH$_3$ (90:10:0.2 followed by 80:20:0.3) as the eluent. The solvent from the pure combined fractions was evaporated off under reduced pressure, the residue was dissolved in ether, and HOAc in ether was added. After 15 h in the refrigerator, white crystals were collected by filtration and dried (60° C., 1 mm Hg) to give 1.5 g (56%) of the title compound: mp 87° C. Purity 99% (HPLC). Fragmenting HPLC analysis supports the stated structure. HRMS m/z calcd for $C_{24}H_{38}N_6O_3$ (M)$^+$ 458.3005. found 458.2988. *Prepared as described in WO 00/76984, Example 192, Step 2.

Example 3

N,N-Dimethyl-2-[(3-{2-[(3-piperazin-1-ylpyrazin-2-yl)oxy]ethoxy}pyridin-2-yl)oxy]ethanamine, trifluoroacetate To a solution of tert-butyl 4-(3-chloropyrazin-2-yl)piperazine-1-carboxylate* (45 mg, 0.15 mmol) and 2-({2-[2-(dimethylamino)ethoxy]pyridin-3-yl}oxy)ethanol (from Example 1, Step 3; 37 mg, 0.16 mmol) in 4 mL of dry methyl tert-butyl ether was 0.2 mL of 1.0 M potassium tert-butoxide in tert-butanol added and the mixture was stirred at room temperature for one week. The reaction mixture was quenched with 2 mL of water. The organic phase was washed with 3×2 mL of 1.0 M NaOH and 2 mL of brine, dried ($MgSO_4$) and concentrated under reduced pressure. The residue was purified with reversed phase chromatography. The purified product was concentrated, redissolved in 3 mL of chloroform, and treated with 0.2 mL of trifluoroacetic acid overnight. The solvent was removed under reduced pressure to give 46 mg (0.092 mmol, 61%) of the title compound as an oil. LC-UV purity 100%. HRMS m/z calc for $C_{19}H_{28}N_6O_3$ $(M)^+$ 388.2223. found 388.2217. *Prepared as described in WO 00/76984, Example 52, Step 1.

Example 4 (Intermediate)

2-Chloro-3-[2-(tetrahydro-2H-pyran-2-yloxy) ethoxy]pyridine

A mixture of 2-chloro-3-hydroxypyridine (5.00 g, 38.6 mmol), 2-(2-bromoethoxy)tetrahydro-2-pyran (5.85 mL, 38.6 mmol) and potassium carbonate (6.40 g, 46.3 mmol) in 200 mL of acetonitrile was heated at reflux overnight. The reaction mixture was filtered, concentrated under reduced pressure and redissolved in 300 mL of ethyl acetate. The organic phase was washed with 3×100 mL of NaOH and 100 mL of brine, dried ($MgSO_4$) and concentrated under reduced pressure. The residue was purified with flash chromatography on a column of silica to give 7.21 g (28.0 mmol, 73%) of the title compound as a yellow oil. LC-UV purity 100%. MS m/z 258 $(M+1)^+$, calc. 258 $(M+1)^+$.

Example 5 (Intermediate)

tert-Butyl (3R)-4-(3-chloropyrazin-2-yl)-3-methylpiperazine-1-carboxylate*

To a solution of 2-chloro-3-[(2R)-2-methylpiperazin-1-yl]pyrazine** (1.59 g, 7.48 mmol) in 200 mL of acetonitrile was boc-anhydride (1.63 g, 7.48 mmol) added in portions over 1 hour. The solution was stirred at room temperature overnight, quenched with 10 mL of water and concentrated. The residue was redissolved in 200 mL of ethyl acetate, washed with 100 mL of 1.0 M $K_2CO_3$, 100 mL of water and 100 mL of brine, dried ($MgSO_4$) and concentrated to give 1.70 g (5.43 mmol, 73%) of the title compound as a colorless oil. LC-UV purity 95%. MS m/z 313 $(M+1)^+$, calc. 313 $(M+1)^{30}$. *Reported in WO 00/76984, Example 172, Step 2. **Reported in WO 00/76984, Example 192, Step 2.

Example 6

2-[(2R)-2-Methylpiperazin-1-yl]-3-[2-({2-[(1-methylpiperidin-4-yl)oxy]pyridin-3-yl}oxy)ethoxy]pyrazine, trifluoroacetate Step 1: 2-({2-[(1-Methylpiperidin-4-yl)oxy]pyridin-3-yl}oxy)ethanol.
A solution of 2-chloro-3-[2-(tetrahydro-2H-pyran-2-yloxy)ethoxy]pyridine (from Example 4; 100 mg, 0.39 mmol), 4-hydroxy-N-methylpiperidine (67 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 62 mg (0.25 mmol, 63%) of the title compound as a colorless oil. LC-UV purity 95%. MS m/z 253 $(M+1)^+$, calc. 253 $(M+1)^+$.

Step 2: 2-[(2R)-2-Methylpiperazin-1-yl]-3-[2-({2-[(1-methylpiperidin-4-yl)oxy]pyridin-3-yl}oxy)ethoxy]pyrazine, trifluoroacetate.
To a solution of 2-({2-[(1-methylpiperidin-4-yl)oxy]pyridin-3-yl}oxy)ethanol (from Step 1; 30 mg, 0.12 mmol) and 1.0 M potassium tert-butoxide in tert-butanol (0.15 mL, 0.15 mmol) in 4 mL of dry toluene was tert-butyl (3R)-4-(3-chloropyrazin-2-yl)-3-methylpiperazine-1-carboxylate (from Example 5; 31 mg, 0.10 mmol) in 1 mL of toluene added. The mixture was shaken at room temperature for 2 days. The reaction mixture was quenched with 2 mL of water. The organic phase was washed with 3×2 mL of water and 2 mL of brine and concentrated under reduced pressure. The residue was purified with reversed phase chromatography. The purified product was concentrated, redissolved in 1 mL of chloroform and treated with 0.2 mL of trifluoroacetic acid for 1 hour. The solvent was removed under reduced pressure to give 36 mg (0.066 mmol, 66%) of the title compound as a brown oil. LC-UV purity 100%. HRMS m/z calcd for $C_{22}H_{32}N_6O_3$ $(M)^+$ 428.2536. found 428.2546.

Example 7

2-[(2R)-2-Methylpiperazin-1-yl]-3-(2-{[2-(2-pyrrolidin-1-ylethoxy)pyridin-3yl]oxy}ethoxy)pyrazine, trifluoroacetate Step 1: 2-{[2-(2-Pyrrolidin-1-ylethoxy)pyridin-3-yl]oxy}ethanol.
A solution of 2-chloro-3-[2-(tetrahydro-2H-pyran-2-yloxy)ethoxy]pyridine (from Example 4; 100 mg, 0.39 mmol), 1-(2-hydroxyethyl)pyrrolidine (68 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 71 mg (0.28 mmol, 72%) of the title compound as a colorless oil. LC-UV purity 95%. MS m/z 253 $(M+1)^+$, calc. 253 $(M+1)^+$.

Step 2: 2-[(2R)-2-Methylpiperazin-1-yl]-3-(2-{[2-(2-pyrrolidin-1-ylethoxy)pyridin-3-yl]oxy}ethoxy)pyrazine, trifluoroacetate.
The procedure in Example 6, Step 2, was followed using 2-{[2-(2-pyrrolidin-1-ylethoxy)pyridin-3-yl]oxy}ethanol (from Step 1; 36 mg, 0.14 mmol) to give 37 mg (0.069 mmol, 69%) of the title compound as a brown oil. LC-UV purity 100%. HRMS m/z calcd for $C_{22}H_{32}N_6O_3$ $(M)^+$ 428.2536. found 428.2551.

Example 8

N,N-Dimethyl-4-({3-[2-({3-[(2R)-2-methylpiperazin-1-yl]pyrazin-2-yl}oxy)ethoxy]pyridin-2-yl}oxy)butan-1-amine, trifluoroacetate Step 1: 2-({2-[4-(Dimethylamino)butoxy]pyridin-3-yl}oxy)ethanol.

A solution of 2-chloro-3-[2-(tetrahydro-2H-pyran-2-yloxy)ethoxy]pyridine (from Example 4; 100 mg, 0.39 mmol), 4-(dimethylamino)-1-butanol (77 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 55 mg (0.22 mmol, 55%) of the title compound as a colorless oil. LC-UV purity 95%. MS m/z 255 (M+1)$^+$, calc. 255 (M+1)$^+$.

Step 2: N,N-Dimethyl-4-({3-[2-({3-[(2R)-2-methylpiperazin-1-yl]pyrazin-2-yl}oxy)ethoxy]pyridin-2-yl}oxy)butan-1-amine, trifluoroacetate.

The procedure in Example 6, Step 2, was followed using 2-({2-[4-(dimethylamino)butoxy]pyridin-3-yl}oxy)ethanol (from Step 1; 29 mg, 0.11 mmol) to give 34 mg (0.062 mmol, 62%) of the title compound as a brown oil. LC-UV purity 100%. HRMS m/z calcd for $C_{22}H_{34}N_6O_3$ (M)$^+$ 430.2692. found 430.2695.

Example 9

2-[(2R)-2-Methylpiperazin-1-yl]-3-[2-({2-[2-(1-methylpyrrolidin-2-yl)ethoxy]pyridin-3-yl}oxy)ethoxy]pyrazine, trifluoroacetate Step 1: 2-({2-[2-(1-Methylpyrrolidin-2-yl)ethoxy]pyridin-3-yl}oxy)ethanol.

A solution of 2-chloro-3-[2-(tetrahydro-2H-pyran-2-yloxy)ethoxy]pyridine (from Example 4; 100 mg, 0.39 mmol), 1-methyl-2-pyrrolidineethanol (79 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 55 mg (0.21 mmol, 53%) of the title compound as a colorless oil. LC-UV purity 95%. MS m/z 267 (M+1)$^+$, calc. 267 (M+1)$^+$.

Step 2: 2-[(2R)-2-Methylpiperazin-1-yl]-3-[2-({2-[2-(1-methylpyrrolidin-2-yl)ethoxy]pyridin-3-yl}oxy)ethoxy]pyrazine, trifluoroacetate.

The procedure in Example 6, Step 2, was followed using 2-({2-[2-(1-methylpyrrolidin-2-yl)ethoxy]pyridin-3-yl}oxy)ethanol (from Step 1; 28 mg, 0.11 mmol) to give 33 mg (0.059 mmol, 59%) of the title compound as a brown oil. LC-UV purity 100%. HRMS m/z calcd for $C_{23}H_{34}N_6O_3$ (M)$^+$ 442.2692. found 442.2681.

Example 10

N-Methyl-N-[2-({3-[2-({3-[(2R)-2-methylpiperazin-1-yl]pyrazin-2-yl}oxy)ethoxy]pyridin-2-yl}oxy)ethyl]propan-2-amine, trifluoroacetate Step 1: 2-[(2-{2-[Isopropyl(methyl)amino]ethoxy}pyridin-3-yl)oxy]ethanol.

A solution of 2-chloro-3-[2-(tetrahydro-2H-pyran-2-yloxy]ethoxy]pyridine (from Example 4; 100 mg, 0.39 mmol), 2-(N-methyl-N-isopropylamino)ethanol (68 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 75 mg (0.30 mmol, 76%) of the title compound as a colorless oil. LC-UV purity 95%. MS m/z 255 (M+1)$^+$, calc. 255 (M+1)$^+$.

Step 2: N-Methyl-N-[2-({3-[2-({3-[(2R)-2-methylpiperazin-1-yl]pyrazin-2-yl}oxy)ethoxy]pyridin-2-yl}oxy)ethyl]propan-2-amine, trifluoroacetate.

The procedure in Example 6, Step 2, was followed using 2-[(2-{2-[isopropyl(methyl)amino]ethoxy}pyridin-3-yl)oxy]ethanol (from Step 1; 40 mg, 0.16 mmol) to give 38 mg (0.070 mmol, 70%) of the title compound as a brown oil. LC-UV purity 100%. HRMS m/z calcd for $C_{22}H_{34}N_6O_3$ (M)$^+$ 430.2692. found 430.2700.

Example 11

N,N-Dimethyl-3-({3-[2-({3-[(2R)-2-methylpiperazin-1-yl]pyrazin-2-yl}oxy)ethoxy]pyridin-2-yl}oxy)propan-1-amine, trifluoroacetate Step 1: 2-({2-[3-(Dimethylamino)propoxy]pyridin-3-yl}oxy)ethanol.

A solution of 2-chloro-3-[2-(tetrahydro-2H-pyran-2-yloxy)ethoxy]pyridine (from Example 4; 100 mg, 0.39 mmol), 3-dimethylamino-1-propanol (69 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 67 mg (0.28 mmol, 71%) of the title compound as a colorless oil. LC-UV purity 95%. MS m/z 241 (M+1)$^+$, calc. 241 (M+1)$^+$.

Step 2: N,N-Dimethyl-3-({3-[2-({3-[(2R)-2-methylpiperazin-1-yl]pyrazin-2-yl}oxy)ethoxy]pyridin-2-yl}oxy)propan-1-amine, trifluoroacetate.

The procedure in Example 6, Step 2, was followed using 2-({2-[3-(dimethylamino)propoxy]pyridin-3-yl}oxy)ethanol (from Step 1; 31 mg, 0.13 mmol) to give 38 mg (0.072 mmol, 72%) of the title compound as a brown oil. LC-UV purity 95%. HRMS m/z calcd for $C_{21}H_{32}N_6O_3$ (M)$^+$ 416.2536. found 416.2523.

Example 12

2-[(2R)-2-Methylpiperazin-1-yl]-3-(2-{[2-(piperidin-3-ylmethoxy)pyridin-3-yl]oxy}ethoxy)pyrazine, trifluoroacetate Step 1: 2-{[2-(Piperidin-3-ylmethoxy)pyridin-3-yl]oxy}ethanol.

A solution of 2-chloro-3-[2-(tetrahydro-2H-pyran-2-yloxy)ethoxy]pyridine (from Example 4; 100 mg, 0.39 mmol), 3-piperidinemethanol (65 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 52 mg (0.21 mmol, 53%) of the title compound as a colorless oil. LC-UV purity 95%. MS m/z 253 $(M+1)^+$, calc. 253 $(M+1)^+$.

Step 2: 2-[(2R)-2-Methylpiperazin-1-yl]-3-(2-{[2-(piperidin-3-ylmethoxy)pyridin-3-yl]oxy}ethoxy)pyrazine, trifluoroacetate.

The procedure in Example 6, Step 2, was followed using 2-{[2-(piperidin-3-ylmethoxy)pyridin-3-yl]oxy}ethanol (from Step 1; 27 mg, 0.11 mmol) to give 37 mg (0.069 mmol, 69%) of the title compound as a brown oil. LC-UV purity 95%. HRMS m/z calcd for $C_{22}H_{32}N_6O_3$ $(M)^+$ 428.2536. found 428.2543.

Example 13

N,N,2-Trimethyl-1-({3-[2-({3-[(2R)-2-methylpiperazin-1-yl]pyrazin-2-yl}oxy)ethoxy]pyridin-2-yl}oxy)propan-2-amine, trifluoroacetate Step 1: 2-({2-[3-(Dimethylamino)-2-methylpropoxy]pyridin-3-yl}oxy)ethanol.

A solution of 2-chloro-3-[2-(tetrahydro-2H-pyran-2-yloxy)ethoxy]pyridine (from Example 4; 100 mg, 0.39 mmol), 2-(dimethylamino)-2-methyl-1-propanol (68 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 79 mg (0.31 mmol, 80%) of the title compound as a colorless oil. LC-UV purity 95%. MS m/z 255 $(M+1)^+$, calc. 255 $(M+1)^+$.

Step 2: N,N,2-Trimethyl-1-({3-[2-({3-[(2R)-2-methylpiperazin-1-yl]pyrazin-2-yl}oxy)ethoxy]pyridin-2-yl}oxy)propan-2-amine, trifluoroacetate.

The procedure in Example 6, Step 2, was followed using 2-({2-[2-(dimethylamino)-2-methylpropoxy]pyridin-3-yl}oxy)ethanol (from Step 1; 38 mg, 0.15 mmol) to give 47 mg (0.086 mmol, 86%) of the title compound as a brown oil. LC-UV purity 95%. HRMS m/z calcd for $C_{22}H_{34}N_6O_3$ $(M)^+$ 430.2692. found 430.2700.

Example 14

2-[(2R)-2-Methylpiperazin-1-yl]-3-{2-[(2-{[(2S)-1-methylpyrrolidin-2-yl]methoxy}pyridin-3-yl)oxy]ethoxy}pyrazine, trifluoroacetate Step 1: 2-[(2-{[(2S)-1-Methylpyrrolidin-2-yl]methoxy}pyridin-3-yl)oxy]ethanol.

A solution of 2-chloro-3-[2-(tetrahydro-2H-pyran-2-yloxy)ethoxy]pyridine (from Example 4; 100 mg, 0.39 mmol), (S)-(−)-2-hydroxymethyl-1-methylpyrrolidine (69 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of water and 2 mL of brine. The organic phase was shaken at 50° C. with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of ethyl acetate. The organic phase was dried ($MgSO_4$) and concentrated under reduced pressure to give 78 mg (0.31 mmol, 79%) of the title compound as a colorless oil. LC-UV purity 95%. MS m/z 253 $(M+1)^+$, calc. 253 $(M+1)^+$.

Step 2: 2-[(2R)-2-Methylpiperazin-1-yl]-3-{2-[(2-{[(2S)-1-methylpyrrolidin-2-yl]methoxy}pyridin-3-yl)oxy]ethoxy}pyrazine trifluoroacetate.

The procedure in Example 6, Step 2, was followed using 2-[(2-{[(2S)-1-methylpyrrolidin-2-yl]methoxy}pyridin-3-yl)oxy]ethanol (from Step 1; 37 mg, 0.15 mmol) to give 39 mg (0.071 mmol, 71%) of the title compound as a brown oil. LC-UV purity 95%. HRMS m/z calcd for $C_{22}H_{32}N_6O_3$ $(M)^+$ 428.2536. found 428.2523.

Example 15

[2-({3-[2-({3-[(2R)-2-Methylpiperazin-1-yl]pyrazin-2-yl}oxy)ethoxy]pyridin-2-yl}oxy)ethyl]amine, trifluoroacetate Step 1: tert-butyl (2-{[3-(2-Hydroxyethoxy)pyridin-2-yl]oxy}ethyl)-carbamate.

A solution of 2-chloro-3-[2-(tetrahydro-2H-pyran-2-yloxy)ethoxy]pyridine (from Example 4; 100 mg, 0.39 mmol), 2-aminoethanol (35 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of 1.0 M NaOH and 1 mL of brine. Di-tert-butyl dicarbonate (94 mg, 0.43 mmol) was added and the reaction was shaken for 2 h and washed with 2×2 mL of NaOH followed by 2×2 mL of water. The organic phase was shaken with 4 mL of 2.0 M acetic acid for 1 week, washed with 4×2 mL of water, 2×2 mL of 1.0 M NaOH and 2 mL of brine, dried ($MgSO_4$) and concentrated under reduced pressure to give 53 mg (0.18 mmol, 46%) of the title compound as a colorless oil. LC-UV purity 90%. MS m/z 299 $(M+1)^+$, calc. 299 $(M+1)^+$.

Step 2: [2-({3-[2-({3-[(2R)-2-Methylpiperazin-1-yl]pyrazin-2-yl}oxy)ethoxy]pyridin-2-yl}oxy)ethyl]amine, trifluoroacetate.

To a solution of tert-butyl (2-{[3-(2-hydroxyethoxy)pyridin-2-yl]oxy}ethyl)carbamate (from Step 1; 44 mg, 0.15 mmol) and 0.22 mL of 1.0 M potassium tert-butoxide in tert-butanol in 4 mL of dry methyl tert-butyl ether was tert-butyl (3R)-4-(3-chloropyrazin-2-yl)-3-methylpiperazine-1-carboxylate (from Example 5; 47 mg, 0.15 mmol)

added and the mixture was shaken at room temperature for 2 days. The reaction mixture was quenched with 2 mL of water. The organic phase was washed with 3×2 mL of water and 2 mL of brine and concentrated under reduced pressure. The residue was purified with reversed phase chromatography. The purified product was concentrated, redissolved in 2 mL of chloroform and treated with 0.2 mL of trifluoroacetic acid for 2 h. The solvent was removed under reduced pressure to give 50 mg (0.10 mmol, 67%) of the title compound as a brown oil. LC-UV purity 100%. HRMS m/z calcd for $C_{18}H_{26}N_6O_3$ $(M)^+$ 374.2066. found 374.2072.

Example 16

N-Methyl)-2-({3-[2-({3-[(2R)-2-methylpiperazin-1-yl]pyrazin-2-yl}oxy)ethoxy]pyridin-2-yl}oxy)ethanamine, trifluoroacetate Step 1: 2-({2-[2-(Methylamino)ethoxy]pyridin-3-yl}oxy) ethanol.

A solution of 2-chloro-3-[2-(tetrahydro-2H-pyran-2-yloxy)ethoxy]pyridine (from Example 4; 100 mg, 0.39 mmol), 2-(methylamino)ethanol (47 µl, 0.58 mmol) and 1.0 M potassium tert-butoxide in tert-butanol (0.8 mL, 0.80 mmol) in 4 mL of toluene was heated at 100° C. for 1 day. The organic phase was washed with 3×2 mL of 1.0 M NaOH and 1 mL of brine. The organic phase was shaken with 4 mL of 2.0 M acetic acid for 2 days. The aqueous phase was washed with 3×3 mL of ethyl acetate, made basic by addition of potassium hydroxide, saturated with sodium chloride and extracted with 3×2 mL of chloroform. The organic phase was dried ($MgSO_4$) and concentrated under reduced pressure to give 12 mg (0.056 mmol, 14%) of the title compound as a colorless oil. LC-UV purity 90%. MS m/z 213 $(M+1)^+$, calc. 213 $(M+1)^+$.

Step 2: N-Methyl-2-({3-[2-({3-[(2R)-2-methylpiperazin-1-yl]pyrazin-2-yl}oxy)ethoxy]pyridin-2-yl}oxy)ethanamine, trifluoroacetate.

To a solution of 2-({2-[2-(methylamino)ethoxy]pyridin-3-yl}oxy)ethanol (from Step 1; 12 mg, 0.056 mmol) and 0.15 mL of 1.0 M potassium tert-butoxide in tert-butanol in 4 mL of dry methyl tert-butyl ether was tert-butyl (3R)-4-(3-chloropyrazin-2-yl)-3-methylpiperazine-1-carboxylate (from Example 5; 18 mg, 0.056 mmol) added and the mixture was stirred at room temperature for 3 days. The reaction mixture was quenched with 2 mL of 1.0 M NaOH. The organic phase was washed with 3×2 mL of 1.0 M NaOH and 1 mL of brine and concentrated under reduced pressure. The residue was purified by reversed phase chromatography. The purified product was concentrated, redissolved in 1 mL of chloroform and treated with 0.2 mL of trifluoroacetic acid for 1 hour. The solvent was removed under reduced pressure to give 32 mg (quantitative yield) of the title compound as a brown oil. LC-UV purity 100%. HRMS m/z calcd for $C_{19}H_{28}N_6O_3$ $(M)^+$ 388.2223. found 388.2231.

Example 17

2-{2-[{2-[2-(Dimethylamino)ethoxy]pyridin-3-yl}oxy]ethoxy}-3-[(2R)-2,4-dimethylpiperazin-1-yl] pyrazine To a solution of 2-{2-[{2-[2-(dimethylamino)ethoxy]pyridin-3-yl}oxy]ethoxy}-3-[(2R)-2-methylpiperazin-1-yl] pyrazine (from Example 1; 0.48 g, 1.19 mmol) in 1,2-dichloroethane (4 mL) was added sodium triacetoxyborohydride (1.3 g, 6.2 mmol) and 37% aqueous formaldehyde (0.072 g, 2.4 mmol), the slightly exothermic reaction was stirred at ambient temperature overnight. Water was added and the mixture was made basic (pH>13) by addition of 8 M NaOH. After being stirred for five minutes, the phases were separated and the aqueous phase was extracted twice with $CHCl_3$. The combined organic phases were dried ($MgSO_4$) and the solvent was removed under reduced pressure. The resulting oil was chromatographed on a column of silica (80 mm, i.d.=30 mm) with $CHCl_3$/MeOH/ $NH_4OH$ (95:5:0.2; 100 mL, followed by 90:10:0.2) as eluent to give 0.33 (67%) of the title compound as a colorless oil. HRMS m/z calcd for $C_{21}H_{32}N_6O_3$ $(M)^+$ 416.2536. found 416.2523.

Example 18

2-[2-(2-[2-(Dimethylamino)ethoxy]phenoxy) ethoxy]-3-[(2R)-2-methylpiperazin-1-yl]pyrazine Step 1: N-{2-[2-(Benzyloxy)phenoxy]ethyl}-N,N-dimethylamine, hydrochloride.*

A mixture of 2-(benzyloxy)phenol (15.2 g, 75.9 mmol), N-(2-chloroethyl)-N,N-dimethylamine hydrochloride (16.4 g, 114 mmol) and potassium carbonate (55 g, 0.40 mol) in dry acetone (200 mL) was heated at reflux. After 3 days (50% conversion according to HPLC), solids were filtered off, the solvent was removed under reduced pressure, and the remaining oil was taken up between $CHCl_3$/0.5 M NaOH. The organic phase was washed once with water and dried. The organic phase (200 mL) was filtered through a plug of silica (60 mm×60 mm), washed with $CHCl_3$ (100 mL) followed by $CHCl_3$/MeOH (95:5; 500 mL). Pure fractions were evaporated under reduced pressure to give 7.7 g of the free base of the title compound as a light brown oil. This material was dissolved in ether and HCl/ether was added to form the hydrochloride salt. This furnished 2.28 g (47%) of the title compound as white crystals: mp 144° C. HRMS m/z calcd for $C_{17}H_{21}NO_2$ $(M)^+$ 271.1572. found 271.1569. *Reported in Bull. Soc. Chim. Fr. 1935, 1737–1741.

Step 2: 2-[2-(Dimethylamino)ethoxy]phenol.*

To a solution of N-{2-[2-(benzyloxy)phenoxy]ethyl}-N, N-dimethylamine (from Step 1; 7.60 g, 28.0 mmol) in MeOH (80 mL) was added 10% Pd/C (0.8 g) and the mixture was hydrogenated at 70 psi and room temperature for 2 h. The reaction mixture was filtered through a pad of Celite® and silica. The solvent was then removed under reduced pressure to give 5.43 g (quantitative yield) of the title compound as off-white crystals: mp 220° C. HRMS m/z calcd for $C_{10}H_{15}NO_2$ $(M)^+$ 181.1103. Found 181.1105. *The corresponding hydrochloride salt has been reported in Bull. Soc. Chim. Fr. 1935, 1737–1741.

Step 3: 2-{2-[2-(Dimethylamino)ethoxy]phenoxy}ethanol.

To dry DMF (50 mL) was added 2-[2-(dimethylamino) ethoxy]phenol (from Step 1; 5.4 g, 28.0 mmol), ethylene carbonate (3.20 g, 36.4 mmol) and potassium carbonate (3.9 g, 28 mmol) and the mixture was heated at 155° C. for one hour 30 minutes. The solvent from the filtered solution was evaporated under reduced pressure and the resulting residue was dissolved in $CHCl_3$ (50 mL) and filtered through a plug of silica (50 mm×50 mm) using $CHCl_3$ (50 mL) followed by $CHCl_3$/MeOH (95:5) as eluents. Solvents from the pure fractions were removed under reduced pressure to give 4.8 g (76%) of the title compound as a light brown oil. HRMS m/z calcd for $C_{12}H_{19}NO_3$ $(M)^+$ 225.1365. found 225.1363.

Step 4: 2-[2-(2-[2-(Dimethylamino)ethoxy]phenoxy)ethoxy]-3-[(2R)-2-methylpiperazin-1-yl]pyrazine.

To a solution of 2-{2-[2-(dimethylamino)ethoxy]phenoxy}ethanol (from Step 3; 0.82 g, 3.6 mmol) in dry DMF (25 mL) was added potassium tert-butoxide (0.59 g, 5.3 mmol) and the mixture was stirred at room temperature for 10 minutes. To the mixture was added 2-chloro-3-[(2R)-2-methylpiperazin-1-yl]pyrazine* (0.70 g, 3.3 mmol) in DMF (5 mL) in one portion and the reaction mixture was stirred at 55° C. for 2 h. A small spoon of silica was added, the solvent was filtered off and the solvent was evaporated under reduced pressure. The crude product was purified on a column of silica (100 mm, i.d.=30 mm) with CHCl$_3$/MeOH/NH$_4$OH (95:5:0.2; 100 mL, followed by 90:10:0.2) as eluent to give 0.80 g (60%) of the title compound as a light brown oil. HRMS m/z calcd for C$_{21}$H$_{31}$N$_5$O$_3$ (M)$^+$ 401.2427. found 401.2414. *Reported in WO 00/76984, Example 192, Step 2.

Example 19

2-{2-[(2-{[2-(Dimethylamino)ethoxy]methyl}pyridin-3-yl)oxy]ethoxy}-3-[(2R)-2-methylpiperazin-1-yl]pyrazine Step 1: {3-[2-(Tetrahydro-2H-pyran-2-yloxy)ethoxy]pyridin-2-yl}methanol.

A suspension of 85% pure 2-(hydroxymethyl)pyridin-3-ol hydrochloride (24.9 g, 130 mmol) and potassium carbonate (60 g, 434 mmol) in acetonitrile (200 mL) was heated at reflux for 15 minutes after which 2-(2-bromoethoxy)tetrahydro-2H-pyran (32.9 g, 160 mmol) was added in one portion and the heating was continued overnight. Solids were filtered off and the solvent was removed under reduced pressure and the resulting oil was chromatographed on a column of silica (100 mm, i.d.=60 mm) with CHCl$_3$ as eluent followed by CHCl$_3$/MeOH/NH$_4$OH (95:5:0.2) to give 28.4 g (93%) of the title compound as a light brown oil. HRMS m/z calcd for C$_{13}$H$_{19}$NO$_4$ (M)$^+$ 253.1314. found 253.1326.

Step 2: {3-[2-(Tetrahydro-2H-pyran-2-yloxy)ethoxy]pyridin-2-yl}methyl methanesulfonate.

To an ice cold solution of {3-[2-(tetrahydro-2H-pyran-2-yloxy)ethoxy]pyridin-2-yl}methanol (from Step 1; 3.39 g, 13.4 mmol) and triethylamine (1.95 g, 19.3 mmol) in dry DCM (25 mL) under an atmosphere of N$_2$ was a solution of methanesulfonic anhydride in DCM (10 mL) added during five minutes. The mixture was stirred at 0° C. for one hour followed by one hour at room temperature. Water (10 mL) was added and the phases were separated. The organic phase was washed once with brine, dried (MgSO$_4$) and the solvent was removed under reduced pressure to give 4.50 g (quantitative yield) of a slightly reddish oil that darkened upon standing. The crude product was used directly in the next step without further purification.

Step 3: N-(2-{[3-(2-(Tetrahydro-2H-pyran-2-yloxy)ethoxy)pyridin-2-yl]methoxy}ethyl)-N,N-dimethylamine.

To a solution of 2-(N,N-dimethylamino)ethanol (0.84 g, 9.4 mmol) in dry dioxane (30 mL) was added potassium tert-butoxide (0.92 g, 8.2 mmol) and the mixture was stirred at room temperature for 20 minutes after which time a solution of {3-[2-(tetrahydro-2H-pyran-2-yloxy)ethoxy]pyridin-2-yl}methyl methanesulfonate (from Step 2; 2.1 g, 6.3 mmol) in dioxane (10 mL) was added. The initially slightly exothermic reaction was stirred at ambient temperature overnight. The solvent from the reaction mixture was evaporated under reduced pressure and the resulting oil was taken up between CHCl$_3$/water. The aqueous phase was extracted once with CHCl$_3$ and the combined organic phases were dried (MgSO$_4$) and the solvent was again evaporated. The resulting oil was chromatographed on a column of silica (100 mm, i.d.=30 mm) with initially CHCl$_3$ 100% (100 mL) followed by CHCl$_3$/MeOH/NH$_4$OH (95:5:0.2; 100 mL, and thereafter 90:10:0.2) to give 0.74 g (36%) of the title compound as a brown oil. HRMS m/z calcd for C$_{17}$H$_{28}$N$_2$O$_4$ (M)$^+$ 324.2049. found 324.2042.

Step 4: 2-[(2-{[2-(Dimethylamino)ethoxy]methyl}pyridin-3-yl)oxy]ethanol.

A solution of N-(2-{[3-(2-(tetrahydro-2H-pyran-2-yloxy)ethoxy)pyridin-2-yl]methoxy}ethyl)-N,N-dimethylamine (from Step 3; 0.69 g, 2.13 mmol) in 2 M HOAc (20 mL) was stirred at 50° C. for two days. The reaction mixture was washed with CHCl$_3$ (×3), saturated with sodium chloride, made basic by addition of 8 M NaOH, and extracted with CHCl$_3$ (×3). The solvent from the combined organic phases was removed under reduced pressure to give 0.47 g (92%) of the title compound as a light brown oil. HRMS m/z calcd for C$_{12}$H$_{20}$N$_2$O$_3$ (M)$^+$ 240.1474. found 240.1476.

Step 5: 2-{2-[(2-{[2-(Dimethylamino)ethoxy]methyl}pyridin-3-yl)oxy]ethoxy}-3-[(2-methylpiperazin-1-yl]pyrazine.

The procedure in Example 18, Step 4, was followed starting from 2-chloro-3-[(2R)-2-methylpiperazin-1-yl]pyrazine* (0.27 g, 1.28 mmol) and 2-[(2-{[2-(dimethylamino)ethoxy]methyl}pyridin-3-yl)oxy]ethanol (from Step 4; 0.28 g, 1.16 mmol). The crude product was purified on a column of silica (100 mm, i.d.=30 mm) with CHCl$_3$/MeOH/NH$_4$OH (80:20:0.5; 200 mL followed by 60:40:1; 100 mL and thereafter 50:50:1) as eluent to give 0.25 g (51%) of the title compound as a light brown oil. HRMS m/z calcd for C$_{21}$H$_{32}$N$_6$O$_3$ (M)$^+$ 417.2536. found 417.2541. *Reported in WO 00/76984, Example 192, Step 2.

Example 20

2-{2-[{2-[(1Z)-3-(Dimethylamino)prop-1-enyl]pyridin-3-yl}oxy]ethoxy}-3-[(2R)-2-methylpiperazin-1-yl]pyrazine Step 1: 3-[2-(Tetrahydro-2H-pyran-2-yloxy)ethoxy]pyridine-2-carbaldehyde.

To a three-necked round flask containing dry DCM (500 mL) cooled down to −78° C. under an atmosphere of N$_2$ was added oxalyl chloride (20.0 mL, 157 mmol) followed by a careful dropwise addition of DMSO (24.5 g, 315 mmol). To the cold reaction mixture was {3-[2-(tetrahydro-2H-pyran-2-yloxy)ethoxy]pyridin-2-yl}methanol (from Example 19, Step 1; 21.0 g, 82.9 mmol) in DCM (25 mL) carefully added, the temperature never exceeded −65° C. After the addition, the reaction mixture was stirred at −78° C. for one hour after which time TEA (50.2 g, 497 mmol) was added and the mixture was stirred another 30 minutes at ambient temperature. To the mixture was added ice water (400 mL) and the organic phase was washed H$_2$O, brine, dried (MgSO$_4$), the brown organic phase was filtered through a pad (60 mm×40 mm) of silica and finally the solvent was removed under reduced pressure to give a brown oil. The hydrated aldehyde was dissolved in toluene (150 mL) and heated for 3 h under Dean-Stark conditions to give 19.9 g (95%) of the title compound as a black oil. HRMS m/z calcd for C$_{13}$H$_{17}$NO$_4$ (M)$^+$ 251.1158. found 251.1153.

Step 2: N,N-dimethyl-N-((2Z)-3-{3-[2-(tetrahydro-2H-pyran-2-yloxy)ethoxy]pyridin-2-yl}prop-2-enyl)amine.

To a suspension of [2-(dimethylamino)ethyl](triphenyl)phosphonium bromide (32.1 g, 77.4 mmol) in dry THF (150 mL) was added a solution of potassium tert-butoxide (9.4 g, 83.7 mmol) in dry t-BuOH (100 mL). The suspension was sonicated for 15 minutes whereafter a solution of 3-[2-(tetrahydro-2H-pyran-2-yloxy)ethoxy]pyridine-2-carbaldehyde (from Step 1; 18.3 g, 72.8 mmol) in THF (30 mL) was added to the yellow suspension and stirred at room temperature for one hour and then for a further hour at 60° C. The solvent was removed under reduced pressure and the residue was mixed with water (0.8 L) and the pH was adjusted to 3–4 with HOAc (~10 mL) and then extracted twice with CHCl$_3$. The aqueous phase was made basic and extracted with CHCl$_3$ (×3), the combined organic phases were dried (MgSO$_4$) and the solvent was removed under reduced pressure. The crude product, consisting of the cis and trans* isomers were separated with preparative HPLC on an YMC ODS-AQ column (30×250 mm) with different gradients of 0.1% TFA in water/CH$_3$CN. The cis isomer was isolated as a light yellow oil (2.33 g, 10%). HRMS m/z calcd for C$_{17}$H$_{26}$N$_2$O$_3$ (M)$^+$ 306.1943. found 306.1942. *The corresponding trans isomer is described in Example 21, Step 1.

Step 3: 2-({2-[(1Z)-3-(Dimethylamino)prop-1-enyl]pyridin-3-yl}oxy)ethanol.

The procedure in Example 19, Step 4, was followed using N,N-dimethyl-N-((2Z)-3-{3-[2-(tetrahydro-2H-pyran-2-yloxy)ethoxy]pyridin-2-yl}prop-2-enyl)amine (from Step 2; 1.3 g, 4.2 mmol) to give 0.86 g (91%) of the title compound as a colorless oil that crystallized upon standing: mp 71° C. HRMS m/z calcd for C$_{12}$H$_{18}$N$_2$O$_2$ (M)$^+$ 222.1368. found 222.1363.

Step 4: 2-{2-[{2-[(1Z)-3-(Dimethylamino)prop-1-enyl]pyridin-3-yl}oxy]ethoxy}-3-[(2R)-methylpiperazin-1-yl]pyrazine.

The procedure in Example 18, Step 4, was followed starting from 2-chloro-3-[(2R)-2-methylpiperazin-1-yl]pyrazine* (0.23 g, 1.0 mmol) and 2-({2-[(1Z)-3-(dimethylamino)prop-1-enyl]pyridin-3-yl}oxy)ethanol (from Step 3; 0.24 g, 1.1 mmol). The crude product was purified on a column of silica (100 mm, i.d.=30 mm) with CHCl$_3$/MeOH/NH$_4$OH (80:20:0.5; 200 mL, followed by 60:40:1) as eluent to give 0.050 g (12%) of the title compound as a light brown oil. HRMS m/z calcd for C$_{21}$H$_{30}$N$_6$O$_2$ (M)$^+$ 398.2430. found 398.2438. *Reported in WO 00/76984, Example 192, Step 2.

Example 21

2-{2-[{2-[(1E)-3-(Dimethylamino)prop-1-enyl]pyridin-3-yl}oxy]ethoxy}-3-[(2R)-2-methylpiperazin-1-yl]pyrazine Step 1: N,N-dimethyl-N-((2E)-3-{3-[2-(tetrahydro-2H-pyran-2-yloxy)ethoxy]pyridin-2-yl}prop-2-enyl)amine.

The title trans isomer compound was isolated as a light yellow oil (1.2 g, 5.5%) from the reaction performed in Example 20, Step 2. HRMS m/z calcd for C$_{17}$H$_{26}$N$_2$O$_3$ (M)$^+$ 306.1943. found 306.1934.

Step 2: 2-({2-[(1E)-3-(Dimethylamino)prop-1-enyl]pyridin-3-yl}oxy)ethanol.

The procedure in Example 19, Step 4, using N,N-dimethyl-N-((2E)-3-{3-[2-(tetrahydro-2H-pyran-2-yloxy)ethoxy]pyridin-2-yl}prop-2-enyl)amine (from Step 1; 1.0 g, 3.3 mmol) was followed to give 0.83 g (quantitative yield) of the title compound as a light brown oil. HRMS m/z calcd for C$_{12}$H$_{18}$N$_2$O$_2$ (M)$^+$ 222.1368. found 222.1364.

Step 3: 2-{2-[{2-[(1E)-3-(Dimethylamino)prop-1-enyl]pyridin-3-yl}oxy]ethoxy}-3-[(2R)-2-methylpiperazin-1-yl]pyrazine.

The procedure in Example 18, Step 4, was followed starting from 2-chloro-3-[(2R)-2-methylpiperazin-1-yl]pyrazine* (0.30 g, 1.4 mmol) and 2-({2-[(1E)-3-(dimethylamino)prop-1-enyl]pyridin-3-yl}oxy)ethanol (from Step 2; 0.32 g, 1.5 mmol). The crude product was purified on a column of silica (100 mm, i.d.=30 mm) with CHCl$_3$/MeOH/NH$_4$OH (80:20:0.5; 200 mL, followed by 60:40:1) as eluent to give 0.030 g (5.5%) of the title compound as a light brown oil. HRMS m/z calcd for C$_{21}$H$_{30}$N$_6$O$_2$ (M)$^+$ 398.2430. found 398.2433. *Reported in WO 00/76984, Example 192, Step 2.

Example 22

2-{2-[{2-[3-(Dimethylamino)propyl]pyridin-3-yl}oxy]ethoxy}-3-[(2R)-2-methylpiperazin-1-yl]pyrazine Step 1: 2-({2-[3-(Dimethylamino)propyl]pyridin-3-yl}oxy)ethanol.

To a mixture of the cis and trans isomers N,N-dimethyl-N-((2E and 2Z)-3-{3-[2-(tetrahydro-2H-pyran-2-yloxy)ethoxy]pyridin-2-yl}prop-2-enyl)amine (from Example 20, Step 2; 3.1 g, 10.1 mmol) in MeOH (50 mL) was added 10% Pd/C (0.30 g) and the mixture was hydrogenated in a Parr apparatus at room temperature at 70 psi H$_2$ overnight. The solvent from the filtered solution was removed under reduced pressure and the tetrahydropyranyl protecting group was removed using the procedure described in Example 19, Step 4, to yield 1.29 g (57%) of the title compound as a brown oil. HRMS m/z calcd for C$_{12}$H$_{20}$N$_2$O$_2$ (M)$^+$ 224.1525. found 224.1521.

Step 2: 2-{2-[{2-[3-(Dimethylamino)propyl]pyridin-3-yl}oxy]ethoxy}-3-[(2R)-2-methylpiperazin-1-yl]pyrazine.

The procedure in Example 18, Step 4, starting from 2-chloro-3-[(2R)-2-methylpiperazin-1-yl]pyrazine* (0.48 g, 2.28 mmol) and 2-({2-[3-(dimethylamino)propyl]pyridin-3-yl}oxy)ethanol (from Step 1; 0.46 g, 2.07 mmol) was followed. The crude product was purified on a column of silica (100 mm, i.d.=30 mm) with CHCl$_3$/MeOH/NH$_4$OH (80:20:0.5; 200 mL, followed by 60:40:1) as eluent to give 0.48 g (58%) of the title compound as a colorless oil. HRMS m/z calcd for C$_{21}$H$_{32}$N$_6$O$_2$ (M)$^+$ 400.2587. found 400.2571. *Reported in WO 00/76984, Example 192, Step 2.

Example 23

{2-[2-({3-[2-({3-[(2R)-2-Methylpiperazin-1-yl]pyrazin-2-yl}oxy)ethoxy]pyridin-2-yl}oxy)ethoxy]ethyl}amine, bis(trifluoroacetate)

Step 1: tert-Butyl {2-[2-({3-[2-(tetrahydro-2H-pyran-2-yloxy)ethoxy]pyridin-2-yl}oxy)ethoxy]ethyl}carbamate.

2-(2-Aminoethoxy)ethanol (0.45 g, 4.3 mmol) and 2-chloro-3-[2-(tetrahydro-2H-pyran-2-yloxy)ethoxy]pyridine (from Example 4; 1.0 g, 3.9 mmol) was added to a solution of potassium tert-butoxide (0.52 g, 4.7 mmol) in dry DMSO (4 mL). The mixture was heated at 90° C. for five minutes. After this time, the reaction mixture was cooled to ambient temperature. Di-tert-butyl dicarbonate (1.1 g, 5.0 mmol) was added and the resulting mixture was stirred for one hour at room temperature. Pyridine (0.3 mL) was added and the mixture left at room temperature over night. The reaction mixture was diluted with water (10 mL) and extracted with CHCl$_3$ (×3), the combined organic phases were dried (MgSO$_4$) and the solvent was removed under reduced pressure. The remaining oil was chromatographed on a column of silica with DCM/MeOH (98:2) as eluent to give 0.76 g (46%) of the title compound as a colorless oil. LC-UV purity: system (A) 96%. HRMS m/z calcd for C$_{21}$H$_{34}$N$_2$O$_7$ (M)$^+$ 426.2366. found 426.2355.

Step 2: tert-Butyl (3R)-4-[3-(2-{[2-(2-{2-[(tert-butoxycarbonyl)amino]ethoxy}-ethoxy)pyridin-3-yl]oxy}ethoxy)pyrazin-2-yl]-3-methylpiperazine-1-carboxylate. tert-Butyl {2-[2-({3-[2-(tetrahydro-2H-pyran-2-yloxy)ethoxy]pyridin-2-yl}oxy)ethoxy]ethyl}carbamate (from Step 1; 0.74 g, 1.7 mmol) was suspended in 2 M HOAc (5 mL) and acetonitrile (1 mL) and heated at 50° C. for two days. The solution was neutralized with concentrated aqueous ammonia. Brine was added (3 mL) and the mixture was extracted with CHCl$_3$ (×3). The combined organic phases were dried (MgSO$_4$) and the solvent was removed under reduced pressure. The remaining oil was dissolved in dry DMSO (10 mL), potassium tert-butoxide (0.36 g, 3.2 mmol) was added followed by tert-butyl (3R)-4-(3-chloropyrazin-2-yl)-3-methylpiperazine-1-carboxylate (from Example 5; 0.59 g, 1.9 mmol) and the mixture was heated at 50° C. for 20 minutes. The reaction mixture was diluted with water/brine (90:10) and extracted with CHCl$_3$ (×3). The combined organic phases were dried (MgSO$_4$), the solvent was removed under reduced pressure and the remaining oil was chromatographed on a column of silica with hexane/EtOAc (70:30) as eluent to give 0.43 g (40%) of the title compound as a colorless oil. LC-UV purity: system (A) 100%. HRMS m/z calcd for C$_{30}$H$_{46}$N$_6$O$_8$ (M)$^+$ 618.3377. found 618.3381.

Step 3: {2-[2-({3-[2-({3-[(2R)-2-Methylpiperazin-1-yl]pyrazin-2-yl}oxy)ethoxy]pyridin-2-yl}oxy)ethoxy]ethyl}amine, bis(trifluoroacetate).

A solution of tert-butyl (3R)-4-[3-(2-{[2-(2-{2-[(tert-butoxycarbonyl)amino]ethoxy}ethoxy)pyridin-3-yl]oxy}ethoxy)pyrazin-2-yl]-3-methylpiperazine-1-carboxylate (from Step 2; 0.405 g, 0.655 mmol) in DCM/TFA (1:1; 4 mL) was stirred at room temperature over night. The solvent was removed under reduced pressure and the remaining oil was dried (1 mm Hg, 40° C.) over night to give 0.424 g (100%) of the title compound as a brown oil. LC-UV purity: system (A) 99%, (B) 98%. HRMS m/z calcd for C$_{20}$H$_{30}$N$_6$O$_4$ (M)$^+$ 418.2329. found 418.2337.

Example 24

[6-({3-[2-({3-[(2R)-2-Methylpiperazin-1-yl]pyrazin-2-yl}oxy)ethoxy]pyridin-2-yl}oxy)hexyl]amine, trifluoroacetate Step 1: (6-{3-[2-(Tetrahydro-2H-pyran-2-yloxy)-ethoxy]-pyridin-2-yloxy}-hexyl)-carbamic acid tert-butyl ester.

The title compound was prepared according to the procedure in Example 23, Step 1, starting from 2-chloro-3-[2-(tetrahydro-2H-pyran-2-yloxy)ethoxy]pyridine (from Example 4; 1.0 g, 3.9 mmol) and 6-amino-1-hexanol (0.50 g, 4.3 mmol). Yield 1.0 g (58%).

Step 2: [6-({3-[2-({3-[(2R)-2-Methylpiperazin-1-yl]pyrazin-2-yl}oxy)ethocy]pyridin-2-yl}oxy)hexyl]amine, trifluoroacetate.

The title compound was prepared starting from (6-{3-[2-(tetrahydro-2H-pyran-2-yloxy)-ethoxy]-pyridin-2-yloxy}-hexyl)-carbamic acid tert-butyl ester (from Step 1; 1.0 g, 2.3 mmol) by first removing the tetrahydropyranyl protecting group followed by subsequent reaction with tert-butyl (3R)-4-(3-chloropyrazin-2-yl)-3-methylpiperazine-1-carboxylate (from Example 5; 0.73 g, 2.3 mmol) according to the procedure in Example 23, Step 2, followed by N-Boc deprotection according to the procedure in Example 23, Step 3. Yield 62 mg (6%). LC-UV purity: system (A) 97%, (B) 97%. HRMS m/z calcd for C$_{22}$H$_{34}$N$_6$O$_3$ (M)$^+$ 430.2692. found 430.2676.

Example 25

[5-({3-[2-({3-[(2R)-2-Methylpiperazin-1-yl]pyrazin-2-yl}oxy)ethoxy]pyridin-2-yl}oxy)pentyl]amine, bis(trifluoroacetate)

The title compound was prepared analogously to Example 24 by substituting 5-amino-1-pentanol (1.76 g, 17.0 mmol) for 6-amino-1-hexanol. Yield 0.126 g (3%). LC-UV purity: system (A) 98%, (B) 97%. HRMS m/z calcd for C$_{21}$H$_{32}$N$_6$O$_3$ (M)$^+$ 416.2536. found 416.2547.

Example 26

5-({3-[2-({3-[(2R)-2,4-Dimethylpiperazin-1-yl]pyrazin-2-yl}oxy)ethoxy]pyridin-2-yl}oxy)-N,N-dimethylpentan-1-amine

[5-({3-[2-({3-[(2R)-2-methylpiperazin-1-yl]pyrazin-2-yl}oxy)ethoxy]pyridin-2-yl}oxy)pentyl]amine bis(trifluoroacetate) (from Example 25; 0.17 g, 0.26 mmol), 1,2-dichloroethane (5 mL), 37% aqueous formaldehyde (0.13 g, 1.6 mmol) and sodium triacetoxyborohydride (0.66 g, 3.1 mmol) was mixed and the mixture was stirred at 50° C. over night. The reaction mixture was quenched with a few drops of 8 M NaOH, diluted with water and extracted twice with CHCl$_3$. The combined organic phases were dried (Hydromatrix) and evaporated under reduced pressure. The crude oil was purified with a preparative LC-MS system (B) to give 36 mg (30%) of the target compound as a light brown oil. LC-UV purity: system (A) 100%, (B) 100%. HRMS m/z calcd for C$_{24}$H$_{38}$N$_6$O$_3$ (M)$^+$ 458.3005. found 458.3013.

Example 27

2-[(2R)-2-Methylpiperazin-1-yl]-3-(2-{[2-(2-piperazin-1-ylethoxy)pyridin-3-yl]oxy}ethoxy)pyrazine, trifluoroacetate Step 1: 4-{2-[3-(2-Hydroxy-ethoxy)-pyridin-2-yloxy-]-ethyl}-piperazine-1-carboxylic acid tert-butyl ester.

The title compound was prepared starting from 2-chloro-3-[2-(tetrahydro-2H-pyran-2-yloxy)ethoxy]pyridine (from Example 4; 0.67 g, 2.6 mmol) and tert-butyl 4-(2-hydroxyethyl)piperazine-1-carboxylate (0.66 g, 2.9 mmol) according to the procedure in Example 23, Step 1, followed by removing the tetrahydropyranyl protecting group according to the procedure given in Example 23, Step 2. Yield 0.36 g (38%). MS (ESI+) for C$_{18}$H$_{29}$N$_3$O$_5$ m/z 368.0 (M+H)$^+$.

Step 2: 2-[(2R)-2-Methylpiperazin-1-yl]-3-(2-{[2-(2-piperazin-1-ylethoxy)-pyridin-3-yl]oxy}ethoxy)pyrazine, trifluoroacetate.

The title compound was prepared by reaction of 4-{2-[3-(2-hydroxy-ethoxy)-pyridin-2-yloxy]-ethyl}-piperazine-1-carboxylic acid tert-butyl ester (from Step 1; 0.367 g, 1.00 mmol) with tert-butyl (3R)-4-(3-chloropyrazin-2-yl)-3-methylpiperazine-1-carboxylate (from Example 5; 0.313 g, 1.00 mmol) according to the procedure in Example 23, Step 2, followed by removal of the N-Boc protecting group according to the procedure in Example 23, Step 3. Yield 12 mg (2%). LC-UV purity: system (A) 80%, (B) 85%. HRMS m/z calcd for $C_{22}H_{33}N_7O_3$ $(M)^+$ 443.2645. found 443.2646.

Preparation of a Pharmaceutical Composition

EXAMPLE

Preparation of Tablets

|   | Ingredients | mg/tablet |
|---|---|---|
| 1. | Active compound of Formula (I) | 10.0 |
| 2. | Cellulose, microcrystalline | 57.0 |
| 3. | Calcium hydrogen phosphate | 15.0 |
| 4. | Sodium starch glycolate | 5.0 |
| 5. | Silicon dioxide, colloidal | 0.25 |
| 6. | Magnesium stearate | 0.75 |

The active ingredient 1 is mixed with ingredients 2, 3, 4 and 5 for about 10 minutes. The magnesium stearate is then added, and the resultant mixture is mixed for about 5 minutes and compressed into tablet form with or without film-coating.

Pharmacological Tests

The ability of a compound of the invention to bind or act at specific 5-HT receptor subtypes can be determined using in vitro and in vivo assays known in the art. The biological activity of compounds prepared in the Examples was tested using different tests.

Affinity Assays

The receptor affinity of compounds in the Examples was determined in competition experiments, where the ability of each compound in serial dilution to displace $^3$H-labelled 5-HT, bound to membranes prepared from a transfected HEK293 cell line stably expressing the human $5\text{-HT}_{2C}$ receptor protein, was monitored by Scintillation Proximity Assay technology. Non-specific binding was defined using 5 µM mianserin. Results obtained for exemplary compounds of the invention are illustrated below.

The binding affinities of the compounds for the human $5\text{-HT}_{2A}$ and $5\text{-HT}_{2B}$ receptors in CHO cell lines were determined using $^3$H-labelled lysergic acid diethyl amide (LSD) and 5-HT, respectively, as radioligands. The binding affinities of the compounds for the human 5-HT1A and $5\text{-HT}_{1B}$ receptors in CHO cell lines were determined similarly using $^3$H-labelled 8-hydroxy-2-(di-n-propylamino)tetralin (8-OH-DPAT) and 5-HT, respectively, as radioligands.

In Vitro Functional Assays

The agonist efficacy at the $5\text{-HT}_{2C}$ receptor of the compounds in the Examples was determined by the ability of each compound to mobilise intracellular calcium in transfected HEK293 cells, stably expressing the human $5\text{-HT}_{2C}$ receptor protein, using the calcium-chelating fluorescent dye FLUO-3 (Sigma, St. Louis, Mo., U.S.A.).

The ability of the compounds to mobilise intracellular calcium at the $5HT_{2A}$ and 5-HT2B receptors was determined similarly using CHO cells expressing the human $5\text{-HT}_{2A}$ or human $5\text{-HT}_{2B}$ receptors.

The maximum functional responses of the compounds, at 1 µM, at the $5\text{-HT}_{2A}$, 5-HT2B and $5\text{-HT}_{2C}$ receptors are expressed relative to the maximum response of 5-HT (serotonin) at a concentration of 1 µM.

Example 28

Test compound was Example 1. Affinity (Ki) was determined using three separate weightings, analyzed on two different occasions, except for the $5\text{-HT}_{2C}$ values which are based on three separate weighings, analyzed on three different occasions (12 individual Ki-values). $EC_{50}$ (the concentration at which a half-maximal effect occurs) and % efficacy are from 2–5 determinations.

|  | $5\text{-HT}_{2A}$ | $5\text{-HT}_{2B}$ | $5\text{-HT}_{2C}$ | $5\text{-HT}_{1A}$ | $5\text{-HT}_{1B}$ |
|---|---|---|---|---|---|
| Ki (nM) | >1000 | >1000 | 12 | 800 | >1000 |
| $EC_{50}$ (nM) | 1200 | 1940 | 4.2 |  |  |
| Efficacy | 14 | 16 | 117 |  |  |

Example 29

Test compound was Example 2. Affinity (Ki) was determined using three separate weightings. $EC_{50}$ and % efficacy are from 3–4 determinations.

|  | $5\text{-HT}_{2A}$ | $5\text{-HT}_{2B}$ | $5\text{-HT}_{2C}$ | $5\text{-HT}_{1A}$ | $5\text{-HT}_{1B}$ |
|---|---|---|---|---|---|
| Ki (nM) | >1000 | >1000 | 10 | 380 | 200 |
| $EC_{50}$ (nM) | 260 | 900 | 3.9 |  |  |
| Efficacy | 40 | 33 | 111 |  |  |

The receptor affinity of some compounds as described in WO 00/76984 are given below.

Example 177 of WO 00/76984

|  | $5\text{-HT}_{2A}$ | $5\text{-HT}_{2B}$ | $5\text{-HT}_{2C}$ | $5\text{-HT}_{1A}$ | $5\text{-HT}_{1B}$ |
|---|---|---|---|---|---|
| Ki (nM) | 177 | 530 | 7 | 517 | 1548 |
| Efficacy | 34 | 28 | 95 |  |  |

Example 193 of WO 00/76984

|  | $5\text{-HT}_{2A}$ | $5\text{-HT}_{2B}$ | $5\text{-HT}_{2C}$ | $5\text{-HT}_{1A}$ | $5\text{-HT}_{1B}$ |
|---|---|---|---|---|---|
| Ki (nM) | 498 | 267 | 10 | 155 | 507 |
| Efficacy | 47 | 8 | 112 |  |  |

Example 194 of WO 00/76984

|  | 5-HT$_{2A}$ | 5-HT$_{2B}$ | 5-HT$_{2C}$ | 5-HT$_{1A}$ | 5-HT$_{1B}$ |
|---|---|---|---|---|---|
| Ki (nM) | 234 | 334 | 7 | 567 | >1000 |
| Efficacy | 64 | 21 | 98 | | |

As is evident from comparisons above, the 5-HT$_{2C}$ receptor selectivity (i e the Ki for 5-HT$_{2C}$ compared to 5-HT$_{2A}$ and 5-HT$_{2B}$) of the compounds according to the present invention is unexpectedly high compared to the compounds according to WO 00/76984.

The receptor affinity of some compounds as described in WO 02/40457 are given below.

Example 2 of WO 02/40457

|  | 5-HT$_{2A}$ | 5-HT$_{2B}$ | 5-HT$_{2C}$ | 5-HT$_{1A}$ | 5-HT$_{1B}$ |
|---|---|---|---|---|---|
| Ki (nM) | 787 | 107 | 4 | 28 | 51 |
| Efficacy | 48 | 27 | 74 | | |

Example 5 of WO 02/40457

|  | 5-HT$_{2A}$ | 5-HT$_{2B}$ | 5-HT$_{2C}$ | 5-HT$_{1A}$ | 5-HT$_{1B}$ |
|---|---|---|---|---|---|
| Ki (nM) | >1000 | 89 | 2.4 | 29 | 19 |
| Efficacy | | 41 | 27 | 97 | |

As is evident from comparisons above, the 5-HT$_{2C}$ receptor selectivity (i e the Ki for 5-HT$_{2C}$ compared to 5-HT$_{2B}$, 5-HT$_{1A}$ and 5-HT$_{1B}$) of the compounds according to the present invention is unexpectedly high compared to the compounds according to WO 02/40457.

What is claimed is:

1. A compound of Formula (I):

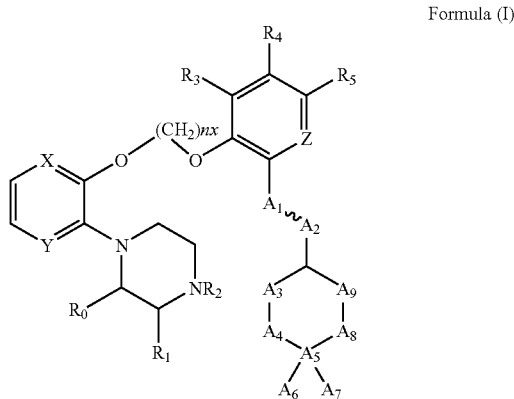

Formula (I)

wherein
nx is 2–4,
R$_0$ and R$_1$ are each independently H or CH$_3$;
R$_2$ is H, C$_1$–C$_4$-alkyl, 2-hydroxyethyl, 2-cyanoethyl or tetrahydropyran-2-yl, C$_1$–C$_4$-acyl or C$_1$–C$_4$-alkoxycarbonyl;
R$_3$–R$_5$ are each independently H, halogen, methyl or methoxy, provided that at least one of R$_3$–R$_5$ is hydrogen;
X, Y, and Z are each independently CH or N;
A$_1$ is O, CH or CH$_2$;
A$_2$ is O, CH or (CH$_2$)$_{n2}$, wherein n2 is an integer 0–2;
the bond between A$_1$ and A$_2$ is a single or double bond;
A$_3$ is (CH$_2$)$_{n3}$, wherein n3 an integer 0–10;
A$_4$ is (CMe$_2$)$_{n4}$, wherein n4 is an integer 0–1;
A$_5$ is N or O;
A$_6$ and A$_7$ are each independently H, C$_1$–C$_4$-alkyl, amino-C$_2$–C$_4$-alkyl, N,N-di-C$_1$–C$_4$-alkylamino-C$_2$–C$_4$-alkyl, C$_3$–C$_6$-cycloalkyl; or when A$_5$ is nitrogen, A$_6$ and A$_7$ together with A$_5$ form a saturated heterocyclic ring;
A$_8$ is (CH$_2$)$_{n8}$, wherein n8 is an integer 0–2;
A$_9$ is H or CH$_2$;
or pharmaceutically acceptable salts, hydrates, geometrical isomers, tautomers, optical isomers, and N-oxides thereof; and
provided that when A$_5$ is N, then A$_5$ is substituted by only two of A$_6$, A$_7$ and A$_8$; when A$_5$ is O, then A$_5$ is substituted by only one of A$_6$, A$_7$ and A$_8$; and when A$_9$ is H, then A$_8$ is not a single bond between A$_5$ and A$_9$.

2. The compound according to claim 1, wherein R$_0$ is methyl.

3. The compound according to any one of claims 1 to 2, wherein the carbon atom, to which the said methyl group R$_0$ is attached, is in the (R)-configuration.

4. The compound according to claim 1, wherein R$_0$ is hydrogen.

5. The compound according to claim 1, wherein R$_1$ is hydrogen.

6. The compound according to claim 1, wherein X and Y both are nitrogen.

7. The compound according to claim 1, wherein R$_2$ is H or methyl.

8. The compound according to claim 1, wherein all of R$_3$–R$_5$ are H.

9. The compound according to claim 1, wherein A$_6$ and A$_7$ are each independently H, methyl, isopropyl, 2-ethylamine or form together a pyrrolidine or piperazine ring.

10. The compound according to claim 1, which has the Formula (Ia):

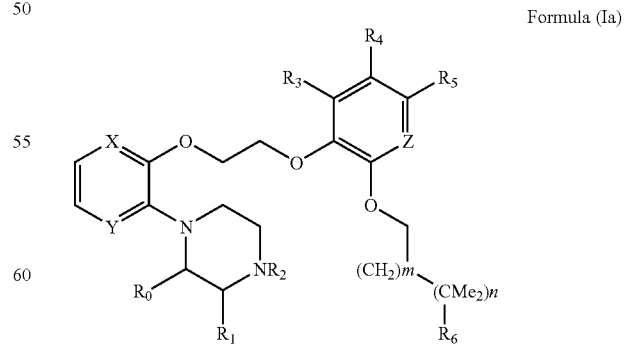

Formula (Ia)

wherein:
R$_0$–R$_5$, X, Y, and Z are as defined in any one of claims 1 to 8, m is an integer 0–10, n is an integer 0 or 1, $R_6$ is $NR_7R_8$ or $OR_9$, wherein $R_7$ and $R_8$ are each independently H or straight or branched $C_1$–$C_4$-alkyl;

or $R_7$ and $R_8$ form together with the nitrogen atom to which they are attached a saturated heterocyclic ring; and $R_9$ is amino-$C_2$–$C_4$-alkyl or N,N-di-$C_1$–$C_4$-alkylamino-$C_2$–$C_4$-alkyl.

11. The compound according to claim 10, wherein $R_7$ and $R_8$ are selected from H, methyl, isopropyl, or form together with the nitrogen atom to which they are attached a pyrrolidine or piperazine ring.

12. The compound according to any one of claims 10 or 11, wherein $R_9$ is 2-aminoethyl.

13. The compound according to claim 10, which compound is:

N,N-Dimethyl-(2-(3-[2-(2-(R)-methyl-3,4,5,6-tetrahydro-2H-[1,2']bipyrazinyl-3'-yloxy)-ethoxy]-pyridin-2-yloxy)-ethyl)-amine;

N,N-Diisopropyl-(2-(3-[2-(2-(R)-methyl-3,4,5,6-tetrahydro-2H-[1,2']bipyrazinyl-3'-yloxy)-ethoxy]-pyridin-2-yloxy)-ethyl)-amine;

N,N-Dimethyl-2-[(3-{2-[(3-piperazin-1-ylpyrazin-2-yl)oxy]ethoxy}pyridin-2-yl)oxy]ethanamine;

2-[(2R)-2-Methylpiperazin-1-yl]-3-(2-{[2-(2-pyrrolidin-1-ylethoxy)pyridin-3-yl]oxy}ethoxy)pyrazine,;

N,N-Dimethyl-4-({3-[2-({3-[(2R)-2-methylpiperazin-1-yl]pyrazin-2-yl}oxy)ethoxy]pyridin-2-yl}oxy)butan-1-amine;

N,N-Methyl-N-[2-({3-[2-({3-[(2R)-2-methylpiperazin-1-yl]pyrazin-2-yl}oxy)ethoxy]pyridin-2-yl}oxy)ethyl]propan-2-amine;

N,N-Dimethyl-3-({3-2-({3-[(2R)-2-methylpiperazin-1-yl]pyrazin-2-yl}oxy)ethoxy-2-yl}oxy)propan-1-amine;

N,N,2-Trimethyl-1-({3-[2-({3-[(2R)-2-methylpiperazin-1-yl]pyrazin-2-yl}oxy)ethoxy]pyridin-2-yl}oxy)propan-2-amine;

[2-({3-[2-({3-[(2R)-2-Methylpiperazin-1-yl]pyrazin-2-yl}oxy)ethoxy]pyridin-2-yl}oxy)ethyl]amine;

N-Methyl-2-({3-[2-({3-[(2R)-2-methylpiperazin-1-yl]pyrazin-2-yl}oxy)ethoxy]pyridin-2-yl}oxy)ethanamine;

2-{2-[{2-[2-(Dimethylamino)ethoxy]pyridin-3-yl}oxy]ethoxy}-3-[(2R)-2,4-dimethylpiperazin-1-yl]pyrazine;

2-[2-(2-[2-(Dimethylamino)ethoxy]phenoxy)ethoxy]-3-[(2R)-2-methylpiperazin-1-yl]pyrazine;

{2-[2-({3-[2-({3-[(2R)-2-Methylpiperazin-1-yl]pyrazin-2-yl}oxy)ethoxy]pyridin-2-yl}oxy)ethoxy]ethyl}amine

[6-({3-[2-({3-[(2R)-2-Methylpiperazin-1-yl]-pyrazin-2-yl}oxy)ethoxy]pyridin-2-yl}oxy)hexyl]amine;

[5-({3-[2-({3-[(2R)-2-Methylpiperazin-1-yl]pyrazin-2-yl}oxy)ethoxy]pyridin-2-yl}oxy)pentyl]amine 5-({3-[2-({3-[(2R)-2,4-Dimethylpiperazin-1-yl]-pyrazin-2-yl}oxy)ethoxy]pyridin-2yl}oxy)-N,N-dimethylpentan-1-amine; or 2-[(2R)-2-Methylpiperazin-1-yl]-3-(2-{[2-(2-piperazin-1-ylethoxy)pyridin-3-yl]oxy}ethoxy)pyrazine.

14. The compound according to any claim 1, which has the Formula (Ib):

Formula (Ib)

wherein:

$R_0$–$R_5$, X, Y, and Z are as in any one of claims 1 to 8, o is an integer 0–2;

p is an integer 0–2, q is an integer 0–1;

$R_{10}$ is H or $C_1$–$C_4$-alkyl.

15. The compound according to claim 14, which compound is:

2-[(2R)-2-Methylpiperazin-1-yl]-3-[2-({2-[(1-methylpiperidin-4-yl)oxy]pyridin-3-yl}oxy)ethoxy]pyrazine, trifluoroacetate;

2-[(2R)-2-Methylpiperazin-1-yl]-3-[2-({2-[2-(1-methylpyrrolidin-2-yl)ethoxy]pyridin-3-yl}oxy)ethoxy]pyrazine, trifluoroacetate;

2-[(2R)-2-Methylpiperazin-1-yl]-3-(2-{[2-(piperidin-3-ylmethoxy)pyridin-3-yl]-oxy}ethoxy)pyrazine, trifluoroacetate;

2-[(2R)-2-Methylpiperazin-1-yl]-3-{2-[(2-{[(2S)-1-methylpyrrolidin-2-yl]-methoxy}pyridin-3-yl)oxy]ethoxy}pyrazine, trifluoroacetate.

16. The compound according to claim 1, which has the Fommia (Ic):

Formula (Ic)

wherein:

$R_0$–$R_5$, X, Y, and Z are as defined above, t is an integer 1–11, the orientation around the double bond may be either cis or trauis;

$R_{11}$ and $R_{12}$ are each independently H or straight or branched $C_1$–$C_4$-alkyl; or $R_{11}$ and $R_{12}$ form together with the nitrogen atom to which they are attached a saturated heterocyclic ring.

17. The compound according to claim 16, wherein $R_{11}$ and $R_{12}$ are both methyl.

18. The compound according to any one of claims 16 or 17, which compound is:
   2-{2-[{2-[(1Z)-3-(Dimethylamino)prop-1-enyl]pyridin-3-yl}oxy]ethoxy}-3-[(2R)-2-methylpiperazin-1-yl]-pyrazine; or
   2-{2-[{2-[(1E)-3-(Dimethylamino)prop-1-enyl]pyridin-3-yl}oxy]ethoxy}-3-[(2-methylpiperazin-1-yl]-pyrazine.

19. The compound according to claim 1, which has the Formula (Id):

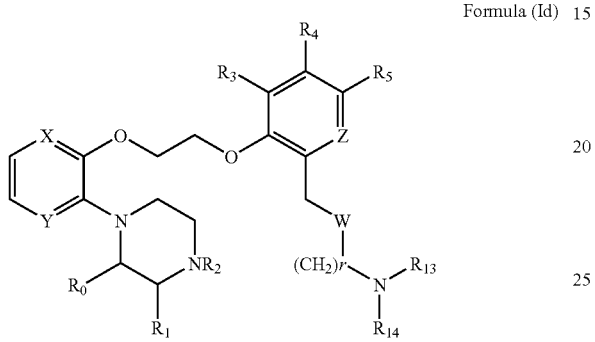

Formula (Id)

wherein:
$R_0$–$R_5$, X, Y, and Z are as defined above,
W is O or $CH_2$;
r is 1–11;
$R_{13}$ and $R_{14}$ are each independently H or straight or branched $C_1$–$C_4$-alkyl; or $R_{13}$ and $R_{14}$ form together with the nitrogen atom to which they are attached a saturated heterocyclic ring.

20. The compound according to claim 19, wherein W is O, X=N, and Y=N.

21. The compound according to claim 19, wherein r=t, W=$CH_2$, X=N, Y=N, $R_{13}$=$R_{11}$ and $R_{14}$=$R_{12}$; where t, $R_{11}$ and $R_{12}$ are as defined for formula (Ic) in claim 16.

22. The compound according to claim 19, wherein $R_{13}$ and $R_{14}$ are both methyl.

23. The compound according to claim 19, which compound is:
   2-{2-[(2-{[2-(Dimethylamino)ethoxy]methyl}pyridin-3-yl)oxy]ethoxy}-3-[(2R)-2-methylpiperazin-1-yl]-pyrazine; or
   2-{2-[{2-[3-(Dimethylamino)propyl]pyridin-3-yl}oxy]ethoxy}-3-[(2R)-2-methylpiperazin-1-yl]-pyrazine.

24. A pharmaceutical composition comprising a compound according to claim 1, as an active ingredient, together with a pharmaceutically acceptable carrier.

25. The compound of claim 1, wherein nx is 2.

26. The compound of claim 1, wherein n3 is 0–7.

27. The compound of claim 1, wherein n3 is 0–5.

28. The compound of claim 10, wherein Z is N.

29. The compound of claim 10, wherein m is 0–7.

30. The compound of claim 10, wherein m is 0–5.

31. The compound of claim 10, wherein the sum of m+n is at least 1.

32. The compound of claim 14, wherein o and p are not both 0.

33. The compound of claim 14, wherein $R_{10}$ is H or methyl.

34. The compound of claim 16, wherein t is an integer 1–8.

35. The compound of claim 16, wherein t is an integer 1–6.

36. The compound of claim 16, wherein t is 1.

37. The compound of claim 19, wherein r is 1–8.

38. The compound of claim 19, wherein r is 1–6.

39. The compound of claim 19, wherein r is 1 and W is $CH_2$.

40. The compound of claim 19, wherein r is 2 and W is O.

* * * * *